(12) United States Patent
Catania et al.

(10) Patent No.: US 7,115,574 B2
(45) Date of Patent: Oct. 3, 2006

(54) SYSTEM AND METHOD FOR SUPPORT LEGACY OPERATING SYSTEM BOOTING IN A LEGACY-FREE SYSTEM

(75) Inventors: Anna P Catania, Milan (IT); James M Lipton, Woodland Hills, CA (US)

(73) Assignee: Zengen, Inc., Woodland Hills, CA (US)

( * ) Notice: Subject to any disclaimer, the term of this patent is extended or adjusted under 35 U.S.C. 154(b) by 645 days.

(21) Appl. No.: 10/015,055

(22) Filed: Dec. 10, 2001

(65) Prior Publication Data

US 2003/0109453 A1  Jun. 12, 2003

(51) Int. Cl.
*A61K 38/00* (2006.01)

(52) U.S. Cl. .............................. 514/18; 514/16; 514/18; 530/327; 530/328

(58) Field of Classification Search .................... 514/14, 514/16, 18; 530/327, 328
See application file for complete search history.

(56) References Cited

U.S. PATENT DOCUMENTS

| | | | |
|---|---|---|---|
| 5,028,592 | A | 7/1991 | Lipton |
| 5,157,023 | A | 10/1992 | Lipton |
| 5,739,111 | A | 4/1998 | Mahe |
| 6,001,812 | A | 12/1999 | Mahe |

FOREIGN PATENT DOCUMENTS

| | | |
|---|---|---|
| EP | 0972 522 A1 | 1/2000 |
| FR | 2784028 | 4/2000 |
| WO | WO 93/01211 | 1/1993 |
| WO | WO/97/10838 | 3/1997 |
| WO | WO/99/58101 | 11/1999 |
| WO | PCT/US00/07846 | 3/2000 |
| WO | WO00/42856 | 7/2000 |

OTHER PUBLICATIONS

U.S. Appl. No. 09/957,765, filed Sep. 21, 2000, Catania et al.
U.S. Appl. No. 09/533,341, filed Mar. 23, 2000, Catania et al.
U.S. Appl. No. 09/535,066, filed Mar. 23, 2000, Lipton.
U.S. Appl. No. 60/200,287, Lipton, filed Apr. 28, 2000.
U.S. Appl. No. 09/774,282, filed Apr. 1996, Mahe.
Airaghi, L., et. al., "Elevated concentrations of plasma α–MSH are associated with reduced disease progression in HIV–infected patients," J. Lab. Clin. Med. 133(3) 309–315 (1999).
Airaghi L, Lettino M, Manfredi MG, Lipton JM, Catania A. Endogenous cytokine antagonists during myocardial ischemia and thrombolytic therapy. Am. Heart J. 130: 204–211, 1995.
Airaghi L. Garofalo L. Cutuli MG. Delgado R. Carlin A. Demitri MT. Badalamenti S. Graziani G. Lipton JM. Catania A. Plasma concentrations of α–melanocyte–stimulating hormone are elevated in patients on chronic haemodialysis. Nephrology Dialysis Transplantation 15:1212–1216, 2000.
Baker, M., et al., "The Relationship between Interleukin–6 and Herpes Simplex Virus Type–1: Implications for Behavior and Immunopathology," *Brain Behav. Immun.* 13(3):201–11 (1999).
Baker, et al., "Principles of Ambulatory Medicine,"*Williams and Wilkins* (1982).
Barcellini, W., et. al., "Inhibitory Influences of α–MSH peptides on HIV–1 expression in Monocytic cells," $12^{th}$ World AIDS Conference Geneva, Abstract No. 60685, Jun. 28–Jul. 3, 1998.
Barcellini W, La Maestra L, Clerici G, Garofalo L, Brini AT, Lipton JM, Catania A. α–MSH peptides inhibit HIV–1 expression in chronically infected promonocytic U1 cells and in acutely infected monocytes. Journal of Leukocyte Biology 68:693–699, 2000.
Bhattacharya A., et al., "Effect of Cyclic AMP on RNA and Protein Synthesis in *Candida albicans,*" *Biochem, Biophysics. Res. Commun.*, 77: 1438–44 (1977).
Bickers, D., Sun–Induced Disorders, *Emergency Medicine Clinics of North America*,3(4): 659–663, 660 (1985).
Capsoni, F., et. al., "Effect of Corticosteriods on Neutrophil Function: Inhibition of Antibody–dependent Cell–Mediated Cytotoxicity (ADCC)," *J. Immunopharmacol.* 5, 217–30 (1983).
Cartledge, J.D., et. al., "Clinically Significant Azole Cross–Resistance in Candida Isolates from HIV–Positive Patients with Oral Candidosis," *AIDS* 11:1839–44 (1997).
Catania, A., et. al., "α–Melanocyte Stimulating Hormone in the Modulation of Host Reactions," *Endocr. Rev.* 14, 564–576 (1993).

(Continued)

*Primary Examiner*—Christopher Tate
*Assistant Examiner*—Roy Teller
(74) *Attorney, Agent, or Firm*—Perkins Coie LLP

(57) ABSTRACT

The invention includes a composition and method of treatment of sinusitis. A preferred embodiment of the invention is a composition for treatment of sinusitis comprising a therapeutically effective amount of one or more peptides selected from the group of peptides with a C-terminal sequence consisting of KPV (SEQ ID NO:1), HFRWGKPV (SEQ ID NO:2), and SYSMEHFRWGKPV (SEQ ID NO:3) used in combination with a therapeutically effective amount of an antihistamine/decongestant, corticosteroid, fungicide and/or antibiotic.

In yet another embodiment of the invention, one or one or more peptides selected from the group of peptides with a C-terminal sequence consisting of KPV (SEQ ID NO:1), HFRWGKPV (SEQ ID NO:2), and SYSMEHFRWGKPV (SEQ ID NO:3), which may or may not be in combination with therapeutically effective amounts of antibiotics, corticosteroids and/or antihistamine/decongestants, are topically or systemically applied to treat sinusitis.

11 Claims, 22 Drawing Sheets

OTHER PUBLICATIONS

Catania, A., et. al., "Melanocortin Peptides Inhibit Production of Proinflammatory Cytokines in Blood of HIV-Infected Patients," *Peptides*, 19(6): 1099–1104 (1998).

Catania, A., et. al., "The Neuropeptide α–MSH in HIV Infection and Other conditions in Humans," *Ann. N.Y. Acad. Sci.* 840: 848–856 (1998).

Catania, A.; et. al., "The Neuropeptide α–MSH has Specific Receptors on Neutrophils and Reduces Chemotaxis in Vitro," *Peptides*17, 675–679 (1996).

Catania A, Airaghi L, Lipton JM. α–MSH in normal human physiology and disease states. Trends Endocrinol. Metab. 11:304–308, 2000.

Catania A, Delgado R, Airaghi L, Cutuli M, Garofalo L, Carlin A, Demitri MT, Lipton JM. α–MSH in systemic inflammation: central and peripheral actions. Annals of the New York Academy of Sciences, 885: 183–187, 1999.

Catania A, Grazia M, Manfredi MG, Airaghi L, Ceriani G, Gandino A, Lipton JM. Cytokine antagonists in infectious and inflammatory disorders. Annals of the New York Academy of Sciences 741: 149–161, 1994.

Catania A, Lipton JM. α—melanocyte–stimulating hormone peptides in host responses: from basic evidence to human research. Annals of the New York Academy of Sciences 680: 412–423, 1993.

Catania A, Cutuli M, Garofalo L, Airaghi L, Valenza, F, Lipton JM, Gattinoni L. Plasma concentrations and anti–L–cytokine effects of α–melanocyte stimulating hormone in septic patients. Crit. Care Med. 28: 1403–1407, 2000.

Catania A, Airaghi L, Motta P, Manfredi MG, Annoni G, Pettenati C, Brambilla F and Lipton JM. Cytokine antagonists in aged subjects and their relation with cellular immunity. Journal of Gerontology: Biological Sciences 52A: B93–97, 1997.

Catania A, Manfredi MG, Airaghi L, Vivirito MC, Capetti A, Milazzo F, Lipton JM and Zanussi C. Plasma concentration of cytokine antagonists in patients with HIV infection. Neuroimmunomodulation 1: 42–49, 1994.

Catania A, Airaghi L, Manfredi MG, Vivirito MC, Milazzo F, Lipton JM, Zanussi C: Proopiomelanocortin–derived peptides and cytokines: relations in patients with acquired immunodeficiency syndrome. Clinical Immunology and Immunopathology 66: 73–79, 1993.

Cavello, J. and Deleo, V., Sunburn, *Dermatologic Clinics*, 4(2):181–187, 181 (1986).

Ceriani, G., et. al., "Central Neurogenic Antiinflammatory Action of α–MSH: Modulation of Peripheral Inflammation Induced by Cytokines and other Mediators of Inflammation," *Neuroendocrinology*, 59:138–143 (1994).

Ceriani G, Diaz J, Murphree S, Catania A, Lipton JM. The neuropeptide alpha–melanocyte–stimulating hormone inhibits experimental arthritis in rats. Neuroimmunomodulation 1:28–32, 1994.

Chiao H, Foster S, Thomas R, Lipton J, and Star RA. α–MSH reduces endotoxin–induced liver inflammation. J. Clin. Invest. 97: 2038–2044, 1996.

Csata, M. et. al., "Enhancement of Candida albicans killing activity of separated human epidermal cells by alpha–melanocyte stimulating hormone," British Journal of Dermatology, 121(1) 145–147 (1989).

Cutuli, M. et. al., "Antimicrobial effects of α–MSH peptides," Journal of Leukocyte Biology 67:233–239 (2000).

Deeter, L.B., et. al., Antipyretic Properties of Centrally Administered α–MSH Fragments in the Rabbit, *Peptides 9*, 1285–1288 (1989).

Delgado, R., et al., "Melanocortin peptides inhibit production of proinflammatory cytokines and nitric oxide by activated microglia," *Journal of Leukocyte Biology*, 63: 740–745 (1998).

Domk–Optiz, I., et. al., "Stimulation of Macrophages by Endotoxin Results in the Reactivation of a Persistent Herpes Simplex Virus Infection," *Scand J. Immunol.* 32(2):69–75 (1990).

Eberle, A. and Schwyzer, R., Hormone–Receptor Interactions, *Clinical Endocrinology* 5, Suppl., 41s–48s (1976).

Eberle, A.N., The Melanotrophins, *Karger, Basel, Switzerland* (1988).

Fauci, A.S., "Host Factors in the Pathogenesis of HIV–induced Disease," *Nature* 384: 529 (1996).

Fitzpatrick, et al., Acute Effects of Ultraviolet Radiation on the Skin: The Sunburn Reaction, *Dermatology in General Medicine*, 4th Edition, 1651–1655, 1651 (1993).

Fitzpatrick, et al., "Color Atlas and Synopsis of Clinical Dermatology," (1983).

Foster, J. Sunburn, *eMedicine—Online Medical Reference Textbook*, (last modified May 1, 2000), <http://emedicine.com/emerg/topic798.htm.

Fox, J. A., et.al., "Immunoreactive α–Melanocyte Stimulating Hormone, Its Distribution in the Gastrointestinal Tract of Intact and Hypophysectomized Rats," *Life. Sci.* 28, 2127–2132 (1981).

Galimberti D, Baron PL, Meda L, Prat E, Scarpini E, Delgado R, Catania A, Lipton JM, Scarlato G. α–MSH peptides inhibit production of nitric oxide and tumor necrosis factor–α by microglial cells activated with β–amyloid and interferon γ. Biochemical Biophysical Research Communications 263: 251–256, 1999.

Getting, et al., POMC Gene–Derived Peptides Activate Melanocortin Type 3 Receptor on Murine Macrophages, Suppress Cytokin Release, and Inhibit Neutrophil Migration in Acute Experimental Inflammation, J. Immunol., vol. 162, No. 12, pp. 7446–7453 (1999).

Harris et al., Alpha–melanocyte stimulating hormone (1–MSH) and Melanin–concentrating hormone (MCH) stimulate phagocytosis by head kidney leucocytes of rainbow trout (*Oncorhynchus mykiss*) in vitro, Fish & Shell Immunol., vol. 8, 8:631–638 (1998).

Gow, N.A., "Germ Tube Growth of *Candida albicans*," *Curr. Topics Med. Myco.* 8, 43–55 (1997).

Hart, D.A., et. al., "*Staphylococcus Aureus* Strains Differ in Their in Vitro Responsiveness to Human Urokinase: Evidence that Methicillin–Resistant Strains are Predominantly Nonresponsive to the Growth–Enhancing Effects of Urokinase," *Can. J. Microbiol.* 42: 1024–31 (1966).

"Harry's Comseticology", *Chemical Publishing, 7$^{th}$ ed.* (1982).

Hiltz, M. E., et. al., "Anti–inflammatory Activity of a COOH–terminal Fragment of the Neuropeptide α–MSH," *FASEB J.* 3, 2282–2284 (1989).

Hiltz, M.E., "Anti–inflammatory Activity of α–MSH (11–13) Analogs: Influences of Alterations in Stereochemistry," *Peptides* 12, 767–71 (1991).

Hiltz, M.E., et. al., "Alpha–MSH Peptodes Inhibit Acute Inflammation and Contact Sensitivity," *Peptides*, 11:979–982 (1990).

Hiltz, M.E., et. al., "α–MSH Peptides Inhibit Acute Inflammation Induced in Mice by rIL–1β, rIL–6, rTNF–α and endogenous pyrogen but not that cause by LTB4, PAF and rIL–8," *Cytokine* 4(4):320–328 (1992).

Holdeman, M., et. al., "Antipyretic Activity of a Potent α–MSH Analog," *Peptides* 6, 273–5 (1985).

Huang, et al., Role of central melanocortins in endotoxin–induced anorexia, Am. J. Physio (Regulatory, Integrative & Comparative Physiology, vol. 276, No. 3, pp. R864–R871 (1999).

Huh S–K, Lipton JM and Batjer HH. The protective effects of α–melanocyte stimulating hormone on canine brainstem ischemia. Neurosurgery 40:132–139, 1997.

Ichiyama T, Sakai T, Catania A, Barsh GS, Furukawa S, Lipton JM. Systemically administered α–melanocyte–stimulating hormone peptides inhibit NF–κB activation in experimental brain inflammation. Brain Research 836: 31–37, 1999.

Ichiyama T, Zhao H, Catania A, Furukawa S, Lipton JM. α–melanocyte–stimulating hormone inhibits NF–κB activation and IαBκ degradation in human glioma cells and in experimental brain inflammation. Experimental Neurology 157:359–365, 1999.

Ichiyama T, Campbell Il, Furukawa S, Catania A, Lipton JM. Autocrine α–melanocyte–stimulating hormone inhibits NF–κB activation in human glioma cells. Journal of Neuroscience Research 58:684–689,1999.

Ichiyama T, Okada K, Campbell IL, Furukawa S, Lipton JM. NF–κB activation is inhibited in human pulmonary epithelial cells transfected with α–melanocyte–stimulating hormone vector. Peptides 21: 1473–1477, 2000.

Ichiyama T, Sakai T, Catania A, Barsh GS, Furukawa S, Lipton JM. Inhibition of peripheral NF–κB activation by central action of α–melanocyte–stimulating hormone. Journal of Neuroimmunology 99: 211–217, 1999.

Lichtensteiger, W ., and Monnet, F., "Differential Response of Dopamine Neurons α–Melanotropin and Analogues in Relation to Their Endocrine and Behavioral Potency," *Life Sci.* 25:2079–2087 (1979).

Lipton, J.M., et.al., "Anti–inflammatory Effects of the Neuropeptide α–MSH in Acute Chronic and Systemic inflammation," *Ann. N.Y. Acad. Sci.* 741, 137–148 (1994).

Lipton, J.M., et. al., "Anti–inflammatory Actions of the Neuroimmunomodulator α–MSH," *Immunol. Today* 18, 140–145 (1997).

Lipton, J.M., "Neuropeptide α–Melanocyte–Stimulating Hormone in Control of Fever, the Acute Phase Response, and Inflammation," *Neuroimmune Networks: Physiology and Diseases*, (Alan R. Liss, Inc. 1989) pp. 243–250.

Lipton, J.M., Modulation of Host Defense by the Neuropeptide α–MSH, *The Yale Journal of Biology and Medicine* 63: 173–182 (1990).

Lipton JM, Catania A, Ichiyama T. Marshalling the anti–inflammtory influence of the neuroimmunomodulator α–MSH. News Physiol. Sci, 15: 192–195, 2000.

Lipton JM, Catania A. The neuropeptide α–MSH: a modulator of host reactions. Seminars in Clinical Immunology 10: 25–29, 1995.

Lipton, et al., Mechanisms of antiinflammatory action of the neuro immunomodulatory peptide alpha–MSH, Annals of the N.Y. Acad. Sci., vol. 840, pp. 373–380 (1998).

Luger, T.A., et. al., "Production of Immunosuppressing Melanotropins by Human Keratinocytes," *Ann. N.Y. Acad. Sci.* 680: 567–570 (1993).

Lyson, K., et. al., "Binding of Anti–Inflammatory α–Melanocyte–Stimulating Hormone Peptides and Proinflammatory Cytokines to Receptors on Melanoma Cells," *Neuroimmunomodulation*, 1:121–126 (1994).

Macaluso, A., et. al., "Antiinflammatory Influences of α–MSH molecules: Central Neurogenic and Peripheral Actions," *The Journal of Neuroscience*, 14(4): 2377–2382 (1994).

Mayhall, Ten Home Remedies for Sunburn, *Seasonal Health*, (Jul. 14, 2000), <http://drkoop.com/wellness/seasonal/summer/sunburn.html>.

Mugridge, K.G., et. al., "α–Melanocyte–Stimulating Hormone reduces interleukin–1β effects on rat stomach preparations possibly through interference with type I receptor," *European Journal of Pharmacology*, 197: 151–155 (1991).

Noisakran S., e. al., "Lymphocytes Delay Kinetics of HSV–1 Reactivation from in vitro Explants of Latent Infected Trigeminal Ganglia," *J. Neuroimmunol.* 95(1–2):126–35 (1999).

Patel, A., et. al., "Herpes Simplex Type 1 Induction of Persistent NF–κB Nuclear Translocation Increases the Efficiency of Virus Replication," *Virology* 247(2):212–22 (1998).

Potts, Sunlight, Sunburn, and Sunscreens, *Postgrad. med.*, 87:52–61 (1990).

Rajora, N., et.al., "α–MSH Modulates Local and Circulating tumor Necrosis Factor α in Experimental Brain Inflammation," *J. Neuroosci*, 17, 2181–2186 (1997).

Rajora, N., et. al., "α–MSH Production Receptors and Influence on Neopterin, in a Human Monocyte/macrophage Cell Line," *J. Leukoc. Biol.* 59, 248–253 (1996).

Rajora N, Boccoli G, Catania A and Lipton JM. α–MSH modulates experimental inflammatory bowel disease. Peptides 18:381–385, 1997.

Remington's Pharmaceutical Sciences, *Mack Publishing Co., 18th ed.* (1990).

Richards, D.B., et. al., "Effect of a–MSH (11–13) (lysine–proline–valine) on Fever in the Rabbit," *Peptides* 5, 815–817 (1984).

*Robbins Pathologic Basis of Disease* 5th ed., Saunders Co., Philadelphia (1994) p. 335–337, 354–355, 1008, 1037–1038.

Ryan, et al., "Inflammation," *a Scope Publication, The Upjohn Company*, (1977).

Star, R.A., et. al., "Evidence of Autocrine Modulation of Macrophage Nitric Oxide Synthase by α–MSH," *Proc. Nat'l. Acad. Sci. (USA)* 92, 8015–8020 (1995).

Stevens, D.L., "Could Nonsteriodal Anti–inflammatory Drugs (NSAIDs) Enhance Progression of Bacterial Infections to Toxic Shock Syndrome?," *Clin. Infect. Dis.* 21, 977–80 (1997).

Szalay, K.S., et. al., "Structure–activity studies with ACTH/α–MSH fragments on corticosteroid secretion of isolated zona glomerulosa arid fasciculata cells," *Regulatory Peptides*, 11: 187–192 (1985).

Taherzadeh S, Sharma S, Chhajlani V, Gantz I, Rajora N, Demitri MT, Kelly L, Zhao H, Catania A, Lipton JM. α–MSH and its receptors in regulation of tumor necrosis factor–α production by human monocyte/macrophages. Am. J. Physiol. 276: R1289–R1294, 1999.

Thody, A.J., et.al., "MSH Peptides are Present in Mammalian Skin," *Peptides* 4, 813–815 (1983).

Uehara, Y., et. al., "Carboxyl–terminal tripeptide of α–Melanocyte–Stimulating Hormone anagonizes interleukin–1–induced anorexia," *European Journal of Pharmacology*, 220: 119–122 (1992).

van Nispen, J.W. and Greven, H.M., "Structure–Activity Relationships of Peptides Derived From ACTH, β–LPH and MSH With Regard To Avoidance Behavior in Rats," *Pharmac. Ther.* 16: 67–102 (1982).

Walev, I., et.al., "Enhancement by TNF–alpha of Reactivation and Replication of Latent Herpes Simplex Virus from Trigeminal Ganglia of Mice," *Arch Virol.* 140(6):987–92 (1995).

Watanabe T, Hiltz ME, Catania A, Lipton JM. Inhibition of IL–Iβ–induced peripheral inflammation by peripheral and central administration of analogs of the neuropeptide α–MSH. Brain Research Bulletin 32: 311–314, 1993.

Weiss, et al., Corticotropin–peptide regulation of intracellular cyclic–AMP production in cortical neurons in primary culture, J. Neurochem. vol. 45, No. 3, pp. 869–874 (1985).

Wenzel, R.P. and Pfaller, M.A., "Candida Species: Emerging Hospital Bloodstream Pathogens," *Infect. Control. Hosp. Epidemiol.* 12: 523–4 (1991).

Wong, K.Y., et. al., "A Potential Mechanism of Local Anti–inflammatory Action of Alpha–Melanocyte–Stimulating Hormone within the Brain: Modulation of Tumor Necrosis Factor–Alpha Production by Human Astrocytic Cells," *Neuroimmunomodulation*, 4:37–41 (1997).

"Vaginitis," National Institute of Child Health and Human Development—Publications On–line (last modified Jan. 12, 2000).<www.nichd.nih.gov/publications/pubs/vagtoc.html>.

"Tampons and Asbestos, Dioxins, & Toxic Shock Syndrome," FDA Center for Devices and Radiological Health (Jul. 23, 1999), <http://www.fda.gov/cdrh/ocd/tamponsabs.html>.

Khurshid, M.A., et. al., :Staphylococcus aureus with Reduced Susceptibility to Vancomycin—Illinois, 1999, *Morbidity and Mortality Weekly Report*, 48(51): 1165–1167 (2000), <http://www.cdc.gov/epo/mmwr/preview/mmwrhtml/mm4851a1.htm>.

"Women's Health, Urinary Tract Infections: A Patient's Guide to Treatment," *AMA Health Insight, On–Line Health Information For Everyone* (last updated Oct. 30, 1998) <http://www.ama–assn.org/insight/h_focus/wom_hlth/uti/uti.htm>.

A

B

C

D

SEQUENCE LISTING

```
<160> NUMBER OF SEQ ID NOS: 12

<210> SEQ ID NO 1
<211> LENGTH: 3
<212> TYPE: PRT
<213> ORGANISM: Artificial Sequence
<220> FEATURE:
<223> OTHER INFORMATION: Designed polypeptide with anti-inflammatory,
      anti-bacterial, anti-fungal and antipyretic properties.

<400> SEQUENCE: 1

Lys Pro Val
1

<210> SEQ ID NO 2
<211> LENGTH: 8
<212> TYPE: PRT
<213> ORGANISM: Artificial Sequence
<220> FEATURE:
<223> OTHER INFORMATION: Designed polypeptide with anti-inflammatory,
      anti-bacterial, anti-fungal and antipyretic properties.

<400> SEQUENCE: 2

His Phe Arg Trp Gly Lys Pro Val
1               5

<210> SEQ ID NO 3
<211> LENGTH: 13
<212> TYPE: PRT
<213> ORGANISM: Homo sapiens

<400> SEQUENCE: 3
```

```
Ser Tyr Ser Met Glu His Phe Arg Trp Gly Lys Pro Val
1               5                   10
```

<210> SEQ ID NO 4
<211> LENGTH: 4
<212> TYPE: PRT
<213> ORGANISM: Artificial Sequence
<220> FEATURE:
<223> OTHER INFORMATION: Designed polypeptide with anti-inflammatory,
      anti-bacterial, anti-fungal and antipyretic properties.

<400> SEQUENCE: 4

Cys Lys Pro Val
1

<210> SEQ ID NO 5
<211> LENGTH: 3
<212> TYPE: PRT
<213> ORGANISM: Artificial Sequence
<220> FEATURE:
<223> OTHER INFORMATION: Designed polypeptide with anti-inflammatory,
      anti-bacterial, anti-fungal and antipyretic properties/Lys is
      DLys.

<400> SEQUENCE: 5

Lys Pro Val
1

<210> SEQ ID NO 6
<211> LENGTH: 3
<212> TYPE: PRT
<213> ORGANISM: Artificial Sequence
<220> FEATURE:
<223> OTHER INFORMATION: Designed polypeptide with anti-inflammatory,
      anti-bacterial, anti-fungal and antipyretic properties/Pro is
      DPro.

<400> SEQUENCE: 6

Lys Pro Val
1

<210> SEQ ID NO 7
<211> LENGTH: 3
<212> TYPE: PRT
<213> ORGANISM: Artificial Sequence
<220> FEATURE:
<223> OTHER INFORMATION: Designed polypeptide with anti-inflammatory,
      anti-bacterial, anti-fungal and antipyretic properties/Val is
      DVal.

<400> SEQUENCE: 7

Lys Pro Val
1

<210> SEQ ID NO 8
<211> LENGTH: 3
<212> TYPE: PRT
<213> ORGANISM: Artificial Sequence
<220> FEATURE:
<223> OTHER INFORMATION: Designed polypeptide with anti-inflammatory,
      anti-bacterial, anti-fungal and antipyretic properties/Lys is
      DLys, Val is DVal.

<400> SEQUENCE: 8

Lys Pro Val
1

<210> SEQ ID NO 9

-continued

```
<211> LENGTH: 39
<212> TYPE: PRT
<213> ORGANISM: Homo sapiens

<400> SEQUENCE: 9

Ser Tyr Ser Met Glu His Phe Arg Trp Gly Lys Pro Val Gly Lys Lys
1               5                   10                  15

Arg Arg Pro Val Lys Val Tyr Pro Ala Gly Glu Asp Asp Glu Ala Ser
            20                  25                  30

Glu Ala Phe Pro Leu Glu Phe
        35

<210> SEQ ID NO 10
<211> LENGTH: 7
<212> TYPE: PRT
<213> ORGANISM: Artificial Sequence
<220> FEATURE:
<223> OTHER INFORMATION: Designed polypeptide with anti-inflammatory,
      anti-microbial, anti-fungal, and anti-viral properties.

<400> SEQUENCE: 10

Met Glu His Phe Arg Trp Gly
1               5

<210> SEQ ID NO 11
<211> LENGTH: 22
<212> TYPE: PRT
<213> ORGANISM: Artificial Sequence
<220> FEATURE:
<223> OTHER INFORMATION: Designed polypeptide with anti-inflammatory,
      anti-microbial, anti-fungal, and anti-viral properties.

<400> SEQUENCE: 11

Arg Pro Val Lys Val Tyr Pro Ala Gly Glu Asp Asp Glu Ala Ser Glu
1               5                   10                  15

Ala Phe Pro Leu Glu Phe
            20

<210> SEQ ID NO 12
<211> LENGTH: 24
<212> TYPE: PRT
<213> ORGANISM: Artificial Sequence
<220> FEATURE:
<223> OTHER INFORMATION: Designed polypeptide with anti-inflammatory,
      anti-microbial, anti-fungal, and anti-viral properties.

<400> SEQUENCE: 12

Ser Tyr Ser Met Glu His Phe Arg Trp Gly Lys Pro Val Gly Lys Lys
1               5                   10                  15

Arg Arg Pro Val Lys Val Tyr Pro
            20
```

SYSTEM AND METHOD FOR SUPPORT LEGACY OPERATING SYSTEM BOOTING IN A LEGACY-FREE SYSTEM

The invention includes a composition and method of treatment of sinusitis. A preferred embodiment of the invention is composition for the treatment of sinusitis comprising a therapeutically effective amount of one or more peptides selected from the group of peptides with a C-terminal sequence consisting of KPV (SEQ ID NO: 1), HFRWGKPV (SEQ ID NO: 2), and SYSMEHFRWGKPV (SEQ ID NO: 3) in combination with a therapeutically effective amount of a antihistamine/decongestant.

BACKGROUND OF THE INVENTION

This invention relates to the field of pathologies of the mucosal membranes of the head and facial sinus cavities caused by inflammation.

Introduction

The sinuses are air pockets located inside the bones in the skull. They are located to either side of the nose (maxillary), behind and in between the eyes (ethmoid), in the forehead (frontal), and there is one much further back in the head (sphenoid). Each sinus is drained by a small hole, about 4 mm in diameter, called an ostium. The sinuses are lined with very fine hair-like projections called cilia. The function of the cilia is to encourage the drainage of mucus.

Sinusitis is frequently caused by an obstructed ostium. This obstruction may result from an anatomical defect such as a deviated septum, inflammation due to an upper respiratory infection or an allergic response, drying of the mucus, or a foreign body caused from an accident. When this occurs, mucus that normally is expelled from the sinus builds up in the sinus causing pain, pressure and an excellent culture medium for bacteria. If the mucus is not cleared immediately, an abscess can develop in the sinus. Unfortunately, draining the abscess is not feasible without doing extensive surgery.

Bacterial Sinusitis

Sinusitis is one of the most common medical problems affecting approximately 30% of the population at some point. The most common pathogens associated with acute sinusitis are *Streptococcus pneumoniae, Haemophilus influenzae*, and *Moraxella catarrhalis*.

Many strains of both *H. influenzae* and *M. catarrhalis* now are beta-lactamase-producing and therefore not susceptible to beta-lactamase antibiotics. Accordingly, broad spectrum antibiotics such as amoxicillin/clavulanate potassium cefuroxime axetil, cefpodoxime proxetil, clarithromycin, and azithromycin are often employed.

The use of decongestants in sinusitis is somewhat controversial. Some authorities to feel that these agents can help to remove the offending matter from the sinus cavities, permitting greater effectiveness for antimicrobial treatment. Others, however, believe that decongestants have no proven role in acute sinusitis and should be avoided because they have side effects and add to the overall cost of treatment. These experts also feel that complicating the therapeutic regimen by having the patient take a decongestant is likely to decrease the likelihood of compliance with the antibiotic treatment.

Chronic sinusitis is defined as sinusitis persisting for at least three weeks. Typically, early in the development of a sinus infection, the cilia are lost and the mucus becomes increasingly thick.

Whereas acute sinusitis is a bacterial infection usually relating to prior viral respiratory tract infection, persistent or chronic sinusitis appears to have a noninfectious etymology. Antimicrobial treatment may clear the condition temporarily, but failure to address and successfully resolve the underlying problem ensures that sinusitis will recur.

A number of conditions can predispose a person to chronic or recurrent sinusitis, including principally, allergic rhinitis. The presentation of chronic sinusitis may be quite subtle, consisting only of congestion, cough, and postnasal drainage; a high index of suspicion is important in identifying possible predisposing factors. The nasal discharge associated with allergic rhinitis is typically clear and watery, and the patient may have symptoms that include itching of the nose and/or eyes.

Among the less common but nonetheless worrisome causes of persistent sinusitis are mechanical obstructions such as polyps or foreign bodies, or mucosal inflammation resulting from disorders such as immunoglobulin deficiencies, cystic fibrosis, and trauma.

Mild cases of chronic sinusitis are usually treated with a regimen of antihistamines/decongestants and/or corticosteroids. Antihistamines may include pseudoephidrine, phenylephrine, phenylpropanolamine, chloropheniramine, bromopheniramine, pheniramine and loratidine. Steroid nasal sprays are commonly used to reduce inflammation in chronic sinusitis. Although these nasal sprays are occasionally used for long-term treatment for patients with chronic sinusitis, the long-term safety of these medications, especially in children, is not fully understood, and the benefits and risks need to be balanced. For patients with severe chronic sinusitis, a doctor may prescribe oral steroids, such as prednisone. Other suitable corticosteroids include betamethasone, cortisone, dexamethasone, hydrocortisone, methylprednisone, and triamcinolone. Because oral steroids can have significant side effects, they are prescribed only when other medications have not been effective. Similar complications exist for antihistamines. Since vascularization of the sinuses is poor, it is difficult to achieve pharmacologically effective concentrations of drugs. As a consequence sinusitis sufferers are often put on lengthy treatments at high dosage, often prescribed in dosages exceeding 2 g per day, from at minimum 2 weeks often extending up to six or eight weeks.

When drug therapies fail to treat the sinusitis, irrigation of saline or saline in combination with antibiotics/antiinflammatories may be applied to treat sinusities of the sinuses immediately downstream from the relevant ostiums passage. If irrigation is ineffective, surgery is often necessary to manually clear the obstructed sinus passages.

Fungal Sinusitis

Research from the Mayo clinic has suggested that sinusitis, especially, chronic sinusitis may have a fungal component to its causation.

Fungal growth was found in washings from the sinuses in 96% of patients with chronic sinusitis. Normal controls had almost as much growth, the difference being that those patients with chronic sinusitis had eosinophiles which had become activated. As a result of the activation, the eosinophiles released Major Basic Protein (MJP) into the mucus, which attacks and kills the fungus but may cause inflammation to the underlying epithelium.

Fungal sinusitis is broken down into several categories: Allergic, Fungus balls (Mycetoma), and Invasive.

Allergic fungal sinusitis (AFS) is commonly caused by *Aspergillus*, as well as *Fusarium, Curvularia*, and others. Patients often have associated asthma. The criteria include CT or MRI confirmation, a dark green or black material the consistency of peanut butter called "allergic mucin" which typically contain a few hyphae, no invasion, and no predisposing systemic disease. Charcot-Leyden crystals, which are breakdown products of eosinophiles are often found. Usually patients are found to be allergic to the fungus, although this is controversial. This disease is analogous to Allergic Bronchopulmonary Aspergilosis.

Fungus balls often involve the maxillary sinus and may present similarly to other causes of sinusitis including helitosis. In addition to radiological abnormalities, thick pus or a clay-like substance is found in the sinuses. There is no allergic mucin, but dense non-innervated hyphae are found. There is an inflammatory response in the mucosa. Upon looking into the sinus, the fungus ball can vary in size from sub-millimeter to the dimensions of the sinus. The fungus balls may have a greenish-black appearance. Removal of the fungus ball is the typical treatment.

Invasive sinusitis can progress rapidly, and typically necessitates surgery, often on an emergency basis and often requiring the intravenous administration of Amphotericin B as well. There have been some forms of invasive sinusitis, which can cause proptosis.

Fungal based sinusitis may be treated with topical fungicides alone or in combination with broad-spectrum antibiotics and corticosteroids. Usually, the fungicide/antibiotic are mixed with a saline irrigation solution and administered as part of irrigation therapy.

Accordingly, it is an object of the present invention to provide a composition and a method of treatment of bacterial and fungal sinusitis while minimizing or eliminating some or all of the complications associated with current antibiotic, anti inflammatory and/or antifungal therapies. It is another object of the present invention to provide a composition and method of treatment effective against chronic and acute sinusitis of either bacterial, fungal or allergic etymology.

SUMMARY OF THE INVENTION

The invention includes a composition and method of treatment of sinusitis. A preferred embodiment of the invention is composition for the treatment of sinusitis comprising a therapeutically effective amount of one or more peptides selected from the group of peptides with a C-terminal sequence consisting of KPV (SEQ ID NO: 1), HFRWGKPV (SEQ ID NO: 2), and SYSMEHFRWGKPV (SEQ ID NO: 3) in combination with a therapeutically effective amount of a antihistamine/decongestant.

Another preferred embodiment of the invention is a composition for the treatment of sinusitis comprising a therapeutically effective amount of one or more of these peptides in combination with a therapeutically effective amount of a corticosteroid.

In another embodiment of the invention each of these compositions may comprise a therapeutically effective amount of an antibiotic.

In another embodiment of the invention each of these combination compositions may further comprise a therapeutically effective amount of a fungicide.

More preferably still, the peptides in each of these preferred combination compositions has the primary sequence of KPV (SEQ ID NO: 1) or VPK-Ac-CC-Ac-KPV (SEQ ID NO: 4) (Ac=Acetyl group). In all the preferred compositions, pharmacologically effective concentrations of the peptides may be as low as $10^{-12}$M but may be as high $10^{-4}$ M.

In another embodiment of the invention a peptide of one or more peptides selected from the group of peptides with a C-terminal sequence consisting of KPV (SEQ ID NO: 1), HFRWGKPV (SEQ ID NO: 2), and SYSMEHFRWGKPV (SEQ ID NO: 3) (SEQ ID NO: 3) is topically or systemically applied to treat sinusitis.

In another embodiment of the invention one or more of these preferred peptides used in combination with therapeutically effective amounts of antihistamines/decongestants, corticosteroids, antibiotics, and/or fungicides, are topically or systemically applied to treat sinusitis.

In yet another embodiment of the invention, one or more peptides selected from the group of peptides with a C-terminal sequence consisting of KPV (SEQ ID NO: 1), HFRWGKPV (SEQ ID NO: 2), and SYSMEHFRWGKPV (SEQ ID NO: 3), which may or may not be in combination with therapeutically effective amounts of antibiotics, corticosteroids, fungicides and/or antihistamine/decongestants, are topically or systemically applied before, during or after surgery to treat sinusitis.

DETAILED DESCRIPTION OF THE INVENTION

Figure 1:
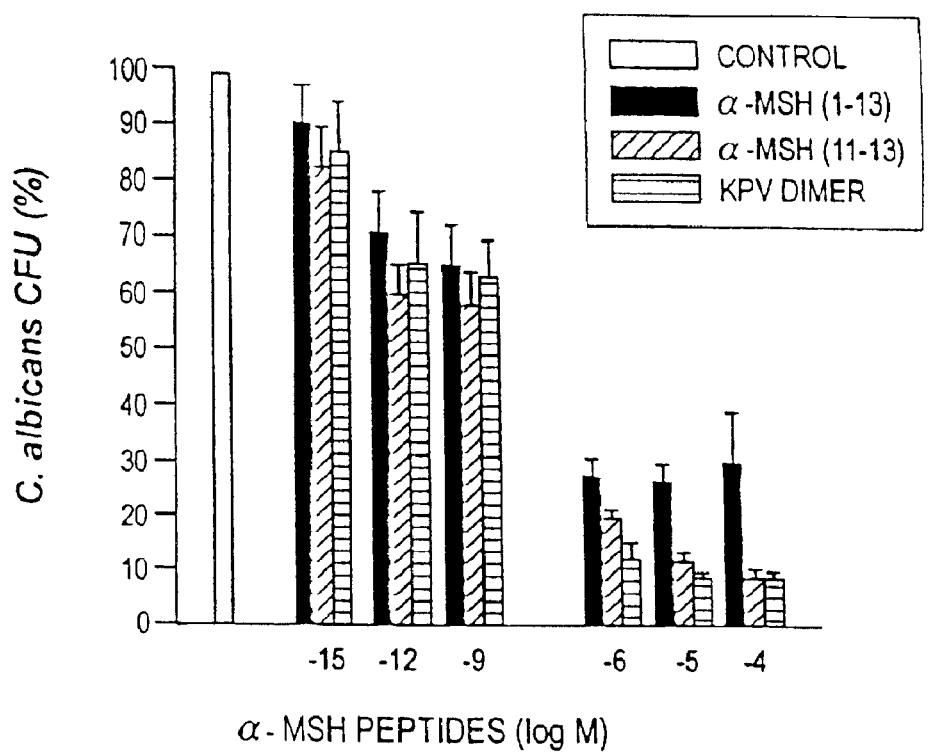
FIG. 1 illustrates the effect of α-MSH(1-13) (SEQ ID NO: 3) and (11-13) (SEQ ID NO: 1) and the peptide VPK-Ac-CC-Ac-KPV (SEQ ID NO: 4) on C. albicans colony forming units compared to controls. All three molecules significantly decreased C. albicans colony forming units over a broad range of peptide concentrations.

The references cited below are hereby incorporated by reference as if fully set forth herein. α-MSH (SEQ ID NO: 3) is a 13 amino acid, anti-inflammatory, anti-fugal peptide with the primary sequence SYSMEHFRWGKPV (SEQ ID NO: 3). In addition to its anti-fungal, anti-inflammatory properties, it also has anti-pyretic properties. The C-terminal trimer, KPV (SEQ ID NO: 1), appears responsible for these properties. Lipton, J. M., Antipyretic and Anti-inflammatory Lys-Pro-Val- Compositions and Methods of Use, U.S. Pat. No. 5,028,592, issued Jul. 2, 1991; Lipton, J. M., Antipyretic and Anti-inflammatory Lys-Pro-Val- Compositions and Methods of Use, U.S. Pat. No. 5,157,023, issued Oct. 20, 1992; Catania, A., Lipton J. M., α-Melanocvte Stimulating Hormone in the Modulation of Host Reactions, 14 *Endocr. Rev.*, 564–576 (1993); Lipton, J. M., Catania, A., Anti-inflammatory Influence of the Neuroimmunomodulator α-MSH, 18 *Immunol. Today,* 140–145 (1997).

The core α-MSH sequence (4-10) (SEQ ID NO: 10) has learning, memory and behavioral effects but limited anti-pyretic and anti-inflammatory activity. Lipton, J. M., Catania, A., *Anti-inflammatory Influence of the Neuroimmunomodulator α-MSH,* 18 *Immunol. Today,* 140–145 (1997). α-MSH, the α-MSH core and its tripeptide C-terminal have very low toxicity. Lipton, J. M., Catania, A., *Anti-inflammatory Influence of the Neuroimmunomodulator α-MSH,* 18 *Immunol. Today,* 140–145 (1997).

α-MSH (SEQ ID NO: 3) is produced by the post translational processing of propriomelanocortin and shares the 1-13 primary sequence with adrenocortitrophic hormone (ACTH) (SEQ ID NO: 9). Eberle, A. N., *The Melanotropins,* Karger, Basel, Switzerland (1988). It is secreted by a wide variety of cell types, including pituitary cells, monocytes, melanocytes, keratinocytes, epidermal cells and the epithelial cells of mucous membranes. Lipton, J. M., Catania, A., *Anti-inflammatory Influence of the Neuroimmunomodulator α-MSH,* 18 *Immunol. Today,* 140–145 (1997); see also Catania et al., unpublished.

α-MSH reduces inflammation and fever by modulating the inflammatory cascade locally and systemically. Rajora, N., Ceriani, G., Catania, A., Star, R. A., Murphy, M. T., Lipton, J. M., α-*MSH Production, Receptors and Influence of Neopterin, in a Human Monocyte/macroghage Cell Line,* 59 *H. Leukoc. Biol.,* 248–253 (1996); Star, R. A., Rajora, N. Huang, J., Stock, R. C., Catania, A., Lipton, J. M., *Evidence of Autocrine Modulation of Macrophage Nitric Oxide Synthase by α-MSH,* 92 *Proc. Natl. Acad. Sci.,* 8016–8020 (1995); Lipton, J. M., Ceriani, G., Macaluso, A., McCoy, D., Carnes, K., Biltz, J., Catania, A., *Anti-inflammatory Effects of the Neuroperptide α-MSH in Acute, Chronic and Systemic Inflammation,* 741 *Ann. N.Y. Acad. Sci.,* 137–148 (1994); Rajora, N., Boccoli, G., Burns, D., Sharma, S., Catania, A., Lipton, J. M., α-*MSH Modulates Local Circulating Tumor Necrosis Factor A in Experimental Brain Inflammation,* 17 *J. Neurosci,* 2181–2186 (1997); Richards, D. B., Lipton, J. M. *Effect of α-MSH* (11-13)(*Lys-Pro-Val*) *on Fever in Rabbits,* 5 *Peptides,* 815–817 (1984); Hiltz, M. E., Lipton, J. M., *Anti-inflammatory Activity of a COOH-terminal Fragment of the Neuropeptide α-MSH,* 3 *FASEB J.,* 2282–2284 (1989).

The broadest aspect of the invention is a composition and method of treatment of pathologies of the facial and maxillary sinuses having an inflammatory and/or fungal component. A preferred embodiment of the invention is composition for the treatment of sinusitis comprising a therapeutically effective amount of one or more peptides selected from the group of peptides with a C-terminal sequence consisting of KPV (SEQ ID NO: 1), HFRWGKPV (SEQ (SEQ ID NO: 2), and SYSMEHFRWGKPV (SEQ ID NO: 3) in combination with a therapeutically effective amount of an antihistamine/decongestant selected from the group consisting of: pseudoephidrine, phenylephrine, phenylpropanolamine, chloropheniramine, bromopheniramine, pheniramine and loratidine.

Another preferred embodiment of the invention is a composition for the treatment of sinusitis comprising a therapeutically effective amount of one or more peptides selected from the group of peptides with a C-terminal sequence consisting of KPV (SEQ ID NO: 1), HFRWGKPV (SEQ ID NO: 2), and SYSMEHFRWGKPV in combination with a therapeutically effective amount of a corticosteroid selected from the group consisting of: betamethasone, cortisone, dexamethasone, hydrocortisone, methylprednisone, prednisone, and triamcinolone.

In another embodiment of the invention each of these compositions may comprise a therapeutically effective amount of an antibiotic selected from the group consisting of amoxicillin, ampicillin, azithramycin, erythromycin, nafcillin, penicillin, amoxicillin/clavulanate potassium, cefuroxime axetil, cefpodoxime proxetil, clarithromycin, and azithromycin.

In another embodiment of the invention each of these combination compositions may further comprise a therapeutically effective amount of a fungicide selected from the group consisting of itraconazole, econazole, ketoconazole, miconazole and fluconazole.

More preferably still, the peptides in each of these preferred combination compositions has the primary sequence of KPV (SEQ ID NO: 1) or VPK-Ac-CC-Ac-KPV (Ac=Acetyl group), In all the preferred compositions, pharmacologically effective concentrations of the peptides may be as low as $10^{-12}$M but may be as high $10^{-4}$ M.

In yet another embodiment of the invention, one or one or more peptides selected from the group of peptides with a C-terminal sequence consisting of KPV (SEQ ID NO: 1), HFRWGKPV (SEQ ID NO: 2), and SYSMEHFRWGKPV, which may or may not be in combination with therapeutically effective amounts of antibiotics, corticosteroids, fungicides and/or antihistamine/decongestants is dissolved in a carrier. Formulations for solution or solids based drug delivery carriers are well known in the art. Such preferred carriers may be selected from the group consisting of saline, phosphate buffered saline, gelatin, maltodextrin, cellulose, microcrystalline cellulose, methyl cellulose and carboxymethyl cellulose.

The formulation of tablets are well known in the art. An exemplary formulation of a hard gelatinous tablet comprises:

| | |
|---|---|
| Gelatine Bloom 30 | 70.0 mg |
| Maltodextrin MD 05 | 108.0 mg |
| di-α-tocopherol | 2.0 mg |
| Sodium ascorbate | 10.0 mg |
| Microcrystalline cellulose | 48.0 mg |

-continued

| | |
|---|---|
| Magnesium stearate | 2.0 mg |
| Active Ingredient | $.2 * 10^{-9}$–$.2 * 10^{-13}$ mg |

An exemplary formulation of a hard tablet comprises:

| | |
|---|---|
| Anhydrous lactose | 130.5 mg |
| Microcrystalline cellulose | 80.0 mg |
| di-α-tocopherol | 2.0 mg |
| Sodium ascorbate | 10.0 mg |
| Polyvinylpyrrolidone K30 | 5.0 mg |
| Magnesium stearate | 2.0 mg |
| Active Ingredient | $.2 * 10^{-9}$–$.2 * 10^{-13}$ mg |

Another embodiment of the invention is a method for the treatment of sinusitis comprising topical or systemic administration of one or more peptides selected from the group of peptides with a C-terminal sequence consisting of KPV (SEQ ID NO: 1), HFRWGKPV (SEQ ID NO: 2), and SYSMEHFRWGKPV (SEQ ID NO: 3). In another preferred method of the invention, one or more of these preferred peptides used in combination with therapeutically effective amounts of antihistamines/decongestants, corticosteroids, antibiotics, and/or fungicides, are topically or systemically applied to treat sinusitis.

In yet another embodiment of the invention, one or one or more peptides selected from the group of peptides with a C-terminal sequence consisting of KPV (SEQ ID NO: 1), HFRWGKPV (SEQ ID NO: 2), and SYSMEHFRWGKPV (SEQ ID NO: 3), which may or may not be in combination with therapeutically effective amounts of antibiotics, corticosteroids, fungicides and/or antihistamine/decongestants, are topically or systemically applied before, during or after surgery to treat sinusitis.

The following examples teach the utility of α-MSH as a fungicide and inflammatory. Methods in microbiology, molecular biology and biochemistry used but not explicitly described in this disclosure are amply described throughout the literature and well within the ability of one skilled in the art.

The peptides used in the following examples include: α-MSH(1-13) (SEQ ID NO: 3), (4-10) (SEQ ID NO: 10), (6-13) (SEQ ID NO: 2), and (11-13) (SEQ ID NO: 1), all of which were N-acetylated and C-amidated, and ACTH(1-39) (SEQ ID NO: 9), and (18-39) (SEQ ID NO: 11) (CLIP). These peptides were prepared by solid-phase peptide synthesis and purified by reversed phased high performance liquid chromatography. Some examples also include a dimer of the amino acid sequence KPV (SEQ ID NO: 1), VPK-Ac-CC-Ac-KPV (SEQ ID NO: 4), which also was N-acetylated and C-amidated (KPV dimer). Dimers can be formed by adding cysteines at the N-termini of any of the above polypeptides and allowing the cysteines of two polypeptides to form a disulfide bond. Both homo-dimers and hetero-dimers can be formed using this method.

C. albicans (clinical isolate) was obtained from the collection of the Department of Microbiology, Ospedale Maggiore di Milano and maintained on Sabouraud's agar slants and periodically transferred to Sabouraud's agar plates and incubated for 48 hours at 28° C. To prepare a stationary growth phase yeast, a colony was taken from the agar plate and transferred into 30 ml Sabouraud-dextrose broth and incubated for 72 hours at 32° C. Cells were centrifuged and suspended in Hank's balanced salt solution ("HBSS") to the desired concentration. Viability, determined by the exclusion of 0.01% methylene blue, remained >98%.

Statistical significance disclosed in the examples below was analyzed using one-way analysis of variance and the Student's t test. Probability values greater than 0.05 were considered significant.

EXAMPLE 1

Example 1 suggests that α-MSH(11-13) (SEQ ID NO: 1), (6-13) (SEQ ID NO: 2) and (1-13) (SEQ ID NO: 3) exhibit similar anti-fungal properties in general and similar anti-candidal properties specifically, as flucanazole over an exceedingly broad range of concentrations and therefore further suggests that α-MSH(11-13) (SEQ ID NO: 1), (6-13) (SEQ ID NO: 2) and (1-13) (SEQ ID NO: 3) may be therapeutic in treating fungal based sinusitis or sinusitis having a fungal component.

C. albicans ($1\times10^6$/ml in HBSS) was incubated in the presence or absence or α-MSH(1-13) (SEQ ID NO: 3) or (11-13) (SEQ ID NO: 1) at concentrations in the range of $10^{-15}$ M to $10^{-6}$ M for 2 hours at 37° C. Cells were then washed in cold distilled water and diluted with HBSS to a concentration of 100 organisms/ml. One-ml aliquots were dispensed on blood agar plates and incubated for 48 hours at 37° C. Organism viability was estimated from the number of colonies formed.

In subsequent experiments using familiar procedures we compared activity of α-MSH(4-10) (SEQ ID NO: 10), (6-13) (SEQ ID NO: 2), (11-13) (SEQ ID NO: 1), ACTH (1-39) (SEQ ID NO: 9), (18-39) (SEQ ID NO: 11) and fluconazole, the latter an established antifungal agent. Melanocortin peptides and fluconazole were tested in concentrations of $10^{-6}$ M to $10^{-4}$ M. There were at least six replicates for each concentration of peptide.

FIG. 1 shows that C. albicans colony forming units (CFU) were greatly reduced by α-MSH(1-13) (SEQ ID NO: 3) and (11-13) (SEQ ID NO: 1). FIG. 1 also shows that the VPK-Ac-CC-Ac-KPV (SEQ ID NO: 4) peptide also inhibited C. albicans colony formation. Concentrations of all three peptides from $10^{-12}$M to $10^{-4}$M had significant inhibitory effects on CFU (p<0.01 vs. control).

Figure 2:
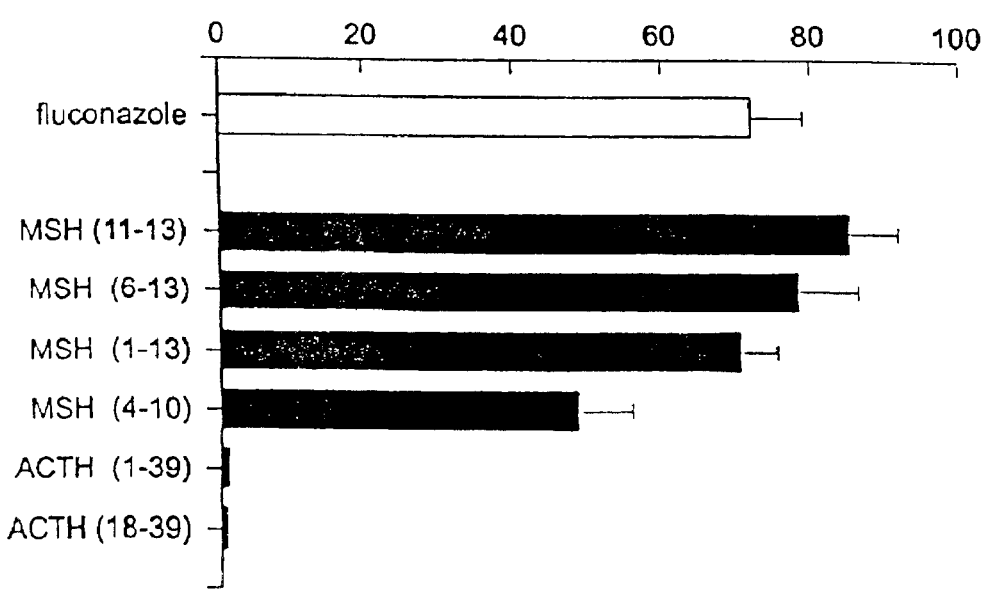
FIG. 2 represents a comparison of candidacidal activity of certain melanocortin peptides and fluconazole (all $10^{-6}$M). The most effective of the melanocortin peptides were those including the C-terminal amino acid sequence of α-MSH, namely, α-MSH(1-13) (SEQ ID NO: 3), (6-13) (SEQ ID NO: 2), and (11-13) (SEQ ID NO: 1).
Figure 3:
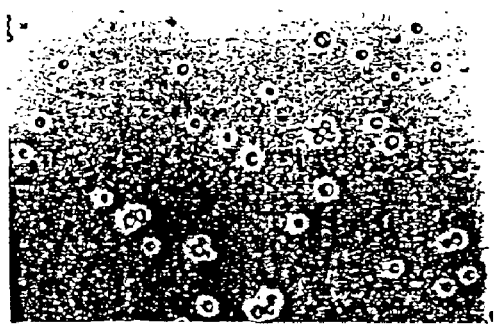
FIG. 3A shows untreated germination of C. albicans, i.e. blastopores.
FIG. 3B shows a horse serum-induced germination of C. albicans.
FIG. 3C shows the effect of α-MSH(1-13) (SEQ ID NO: 3) treatment on germination of C. albicans
FIG. 3D shows the effect of α-MSH(11-13) (SEQ ID NO: 1) treatment on germination of C. albicans
Figure 3:
Figure 3:
Figure 3:

FIG. 2 demonstrates that in experiments comparing the relative potency of $10^{-4}$M melanocortin peptides in reducing C. albicans viability, α-MSH(11-13) (SEQ ID NO: 1), (6-13) (SEQ ID NO: 2), and (1-13) (SEQ ID NO: 3) were the most effective. Their inhibitory activity was similar to that of equimolar fluconazole. The core α-MSH sequence (4-10) (SEQ ID NO: 10), which has behavioral effects but little anti-inflammatory activity, caused approximately 50% inhibition of CFU. FIG. 2 also shows that although this inhibitory effect was substantial (p<0.01 vs. control), it was significantly less than that caused by α-MSH fragments bearing the KPV signal sequence, i.e., α-MSH(6-13) (SEQ ID NO: 2) and (11-13) (SEQ ID NO: 1) (p<0.01), or the parent molecule α-MSH(1-13) (SEQ ID NO: 3), (p<0.05). ACTH(1-39) (SEQ ID NO: 9) and the ACTH fragment (18-39) (SEQ ID NO: 11) did not reduce C. albicans viability. Even higher concentrations of these ACTH (SEQ ID NO: 9) peptides (up to $10^{-4}$M) were likewise ineffective in reducing C. albicans CFU (results not shown in the figures).

These results show that α-MSH(1-13) (SEQ ID NO: 3), its C-terminal tripeptide (11-13) (SEQ ID NO: 1), and other α-MSH fragments have significant fungicidal effects against C. albicans. The most effective of the α-MSH peptides were those including the C-terminal amino acid sequence KPV of the α-MSH sequence, i.e., α-MSH (1-13) (SEQ ID NO: 3), (6-13) (SEQ ID NO: 2), and (11-13) (SEQ ID NO: 1). In addition, the sequence VPK-Ac-CC-Ac-KPV (SEQ ID NO: 4) has also been shown to be at least as effective as α-MSH(11-13) (SEQ ID NO: 1) against microbes. The α-MSH core sequence (4-10) (SEQ ID NO: 10), which is known to influence learning and memory, but has little antipyretic and anti-inflammatory influence, was effective, but less so. The ACTH peptides (1-39) (SEQ ID NO: 9) and (18-39) (SEQ ID NO: 11) did not have significant candidacidal effects α-MSH(1-13), (6-13) and (11-13). These observations indicate that antifungal activity is not common to all melanocortin peptides, but rather is specific to α-MSH amino acid sequences, and most particularly to the C-terminal amino-acid sequences of α-MSH (SEQ ID NO: 3). This strongly suggests that α-MSH(1-13) (SEQ ID NO: 3), its C-terminal tripeptide (11-13) (SEQ ID NO: 1), and other α-MSH fragments could server as a basis for a therapeutic treatment of sinusitis having a fungal component.

EXAMPLE 2

Example 2 demonstrates that α-MSH(1-13) (SEQ ID NO: 3), (6-13) (SEQ ID NO: 2) or (11-13) (SEQ ID NO: 1) strongly inhibits Candidal germination. Accordingly, Example 2 also suggests that α-MSH(1-13) (SEQ ID NO: 3), (6-13) (SEQ ID NO: 2) or (11-13) (SEQ ID NO: 1) may be therapeutic in the treatment of sinusitis having in general a fungal component and specifically having a Candidal component. C. albicans from stationary phase cultures were washed twice with distilled water and suspended in HBSS to a final concentration of $2\times10^6$/ml. Hyphal growth was induced by addition of 10% inactivated horse serum (GIBCO/BRL, Great Britain) to yeast incubated for 45 minutes at 37° C. with continuous shaking. Horse serum was removed by washing cells twice with HBSS and incubation was continued for 60 minutes at 37° C. in the presence of α-MSH(1-13) (SEQ ID NO: 3), (6-13) (SEQ ID NO: 2) or (11-13) (SEQ ID NO: 1) at a concentration of $10^{-6}$M with continuous shaking. The percentage of filamentous cells was evaluated under a light microscope with the aid of hemocytometer. Experiments were run in triplicate and at least 200 cells were scored. Photomicrographs were taken with a MC100 camera attached to an Axioskop Zeiss microscope.

FIGS. 3A–D show that coincubation of C. albicans with α-MSH(1-13) (SEQ ID NO: 3) or (11-13) (SEQ ID NO: 1) inhibited germ tube formation induced by horse serum, α-MSH(1-13) (SEQ ID NO: 3) caused 28–32% reduction in the number of filamentous cells; the tripeptide inhibited germination by 54–58%. The octapeptide α-MSH (6-13) (SEQ ID NO: 2) had similar activity (approximately 50% inhibition)(not shown).

These results show that α-MSH(1-13) (SEQ ID NO: 3), α-MSH(6-13) (SEQ ID NO: 2), and α-MSH(11-13) (SEQ ID NO: 1) all significantly inhibit germination by C. albicans. The infection cycle of C. albicans, and candida in general, begins with adherence of fungal cells to epithelial cells. After adhesion, the fungal cells undergo a switch from ellipsoid blastophore form to various filamentous forms, including germ tubes, pseudohyphae, and hyphae. Gow, N. A., Germ Tube Growth of Candida Albicans, Curr. Topics Med. Mycol. 8, 43–45 (1997). α-MSH peptides were added to C. albicans after promotion of hyphal growth. α-MSH (1-13) (SEQ ID NO: 3) inhibited subsequent germ tube formation by approximately 30%, α-MSH(11-13) (SEQ ID NO: 1) inhibited germ tube formation by approximately 56%, and α-MSH(6-13) (SEQ ID NO: 2) inhibited germ tube formation by approximately 50%. As with the results in example 1, the highest level of inhibition is observed for the tripeptide containing only the C-terminal KPV (SEQ ID NO: 1) amino acid sequence. The results of example 2 suggest that α-MSH(1-13) (SEQ ID NO: 1), fragments of α-MSH (1-13) (SEQ ID NO: 3), or peptides containing the C-terminal KPV (SEQ ID NO: 1) amino acid sequence of the α-MSH peptides could be of therapeutic use not only in the prevention and treatment of early fungal infection as stated in example 1, but also in the treatment of later stage fungal infections. By preventing germination, the α-MSH peptides could prevent the innervation of the epithelial cells that occurs during chronic candidiasis, thus providing a tool to combat long-term fungal infection, particularly fungal infection leading to sinusitis. This therapy would be especially beneficial to immunocompromised patients, who tend to exhibit a high rate of candidal infections.

EXAMPLE 3

Example 3 illustrates that α-MSH (SEQ ID NO: 3) and its derivatives exhibit their anti-fungal properties in general and anti-candidal properties specifically, without compromising the ability of human neutrophils to independently combat Candida. Example 3 further suggests that systemic or topical administration of α-MSH may used to treat fungal based sinusitis in general and candidal based sinusitis specifically. Venous blood (20 ml) from health volunteers was anticoagulated with heparin. Neutrophils were isolated using dextran sedimentation and Ficoll-Hypaque (Sigma Chemical Co., St. Louis, Mich., USA) centrifugation. Erythrocytes were lysed via hypotonic shock. Neutrophils represented at least 97% of the cell suspension. Cell viability, estimated by trypan blue exclusion, was >98%. Neutrophils were suspended to a final concentration in HBSS.

C. albicans ($1 \times 10^6$) were opsonized with human AB serum in a shaking water bath for 30 minutes at 37° C. Organisms were then incubated with neutrophils in medium or in medium with α-MSH(1-13) (SEQ ID NO: 3) or α-MSH(11-13) (SEQ ID NO: 1) in concentrations of $10^{-15}$ M to $10^{-4}$ M in a shaking water bath for 2 hours at 37° C. After incubation, the culture tubes were placed on ice to stop growth and extracellular organisms were washed twice with centrifugation at 1000×g at 4° C. A 2.5% sodium desoxycholate solution was added to obtain a suspension of $10^6$ cells/ml. Two 1/100 serial dilutions in HBSS were made to obtain a final suspension of 100 cells/ml. Aliquots of 1 ml were dispensed on blood agar plates and incubated for 48 hours at 37° C. Colony forming units (CFUs) were counted at the end of the incubation period. Experiments were run in triplicate and repeated using blood from 5 different donors.

Figure 4:
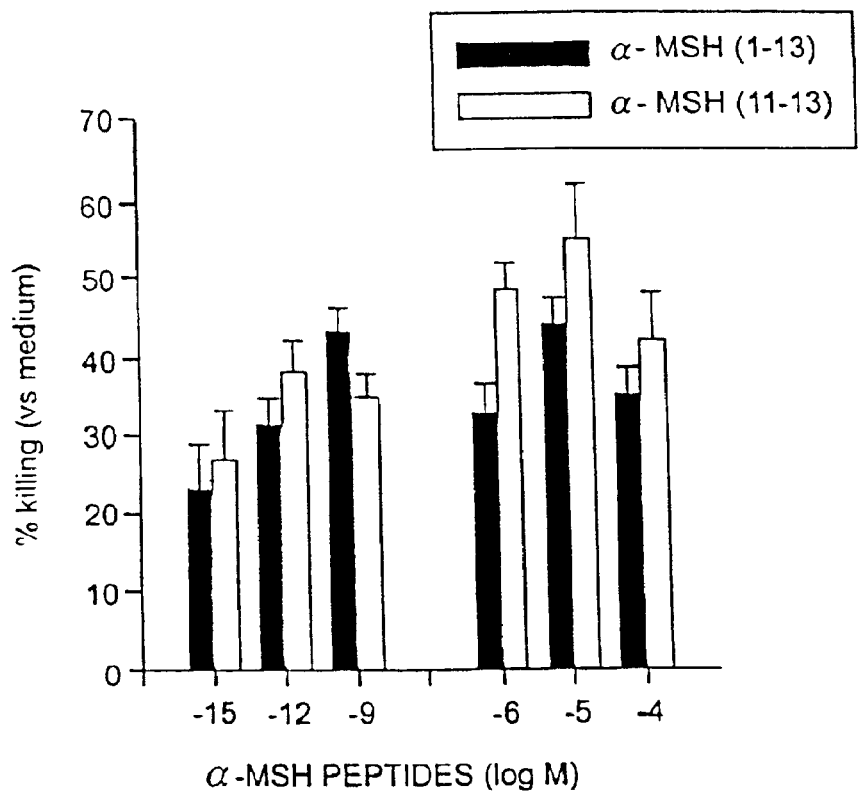
FIG. 4 illustrates the effect of α-MSH(1-13) (SEQ ID NO: 3) and (11-13) (SEQ ID NO: 1) on C. albicans killing by human neutrophils. Values are expressed as percent increase in killing vs. medium along. Scores are means±SEM.

FIG. 4 shows that α-MSH(1-13) (SEQ ID NO: 3) and (11-13) (SEQ ID NO: 1) enhanced the killing of C. albicans by human neutrophils when administered in concentrations of $10^{-12}$M to $10^{-4}$M (p<0.01). Therefore, enhanced killing occurred over a very broad range of concentrations including picomolar concentrations, i.e. the quantity of α-MSH found in human placenta. Catania, A., Airaghi, L., Garofalo, L., Cutuli, M., Lipton, J. M., *The Neuropeptide α-MSH in AIDS and Other Conditions in Humans*, Ann. N.Y. Acad. Sci. 840, 848–856 (1998).

Reduced killing of pathogens is a dire consequence of therapy with corticosteroids and nonsteroidal anti-inflammatory drugs during infection. Stevens, D. L., *Could Nonsteroidal Anti-inflammatory Drugs (NSAIDS) Enhance Progression of Bacterial Infections to Toxic Shock Syndrome?*, Clin. Infect. Dis., 21, 977–80 (1997); Capsoni, F., Meroni, P. L., Zocchi, M. R., Plebani, A. M., Vezio, M., *Effect of Corticosteroids on Neutrophil Function: Inhibition of Antibody-dependent Cell-mediated Cytotoxicity (ADCC)*, J. Immunopharmacol. 5, 217–230 (1983). This effect is particularly dangerous in immunocompromised patients.

These results show that α-MSH(1-13) (SEQ ID NO: 3) and α-MSH(11-13) (SEQ ID NO: 1) do not interfere with the ability of neutrophils to combat fungal infection. Presence of either peptide sequence, at concentrations ranging from $10^{-12}$ M to $10^{-4}$ M, enhanced killing of C. albicans by neutrophils. This is of therapeutic importance because many of the agents used to combat sinusitis, such as corticosteroids and nonsteroidal anti-inflammatories, have a detrimental effect on immune system function. This effect can be especially dangerous to immunocompromised patients. The results from example 3 suggest that the α-MSH peptides can be utilized as antifungal agents (as discussed in example 1 and 2) without inhibiting the ability of neutrophils to combat bacteria and parasites.

EXAMPLE 4

Example 4 suggests a cellular mechanism to explain how α-MSH exerts its anti-fungal properties and further suggests that systemic or topical administrators of α-MSH may be used to treat fungal based sinusitis in general and candidal based sinusitis specifically. C. albicans ($10^6$/ml), permeabilized with toluene/ethanol, were incubated at 37° C. with continuous shaking in the presence of $10^{-6}$ M α-MSH(1-13) (SEQ ID NO: 3), (11-13), (SEQ ID NO: 1), forskolin, an agent known to increase intracellular cAMP, or in medium alone. The reaction was stopped after 3 minutes by the addition of ice cold ethanol, cAMP was measured in duplicate using a commercial enzyme immunoassay (EIA) kit (Amersham, United Kingdom) after extraction via the liquid-phase method according to manufacturer's instructions. The effect of forskolin ($10^{-6}$ M) on C. albicans colony formation was determined using the same procedure as for α-MSH peptides.

Figure 5:
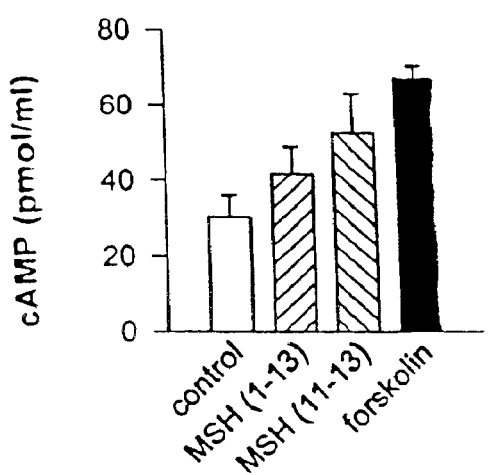
FIG. 5 illustrates the effect of α-MSH(1-13) (SEQ ID NO: 3), (11-13) (SEQ ID NO: 1), and forskolin on cAMP content of C. albicans.
Figure 6:
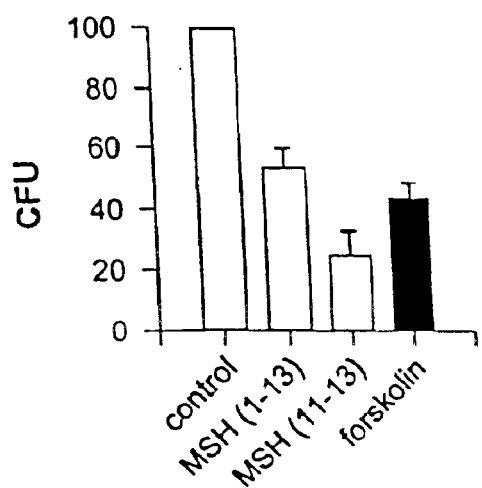
FIG. 6 illustrates the inhibitory effect of α-MSH(1-13) (SEQ ID NO: 3), (11-13) (SEQ ID NO: 1), and forskolin on C. albicans colony forming units.

Because many of the effects of α-MSH are known to be mediated by induction of cAMP, we measured effects of α-MSH peptides on cAMP accumulation in C. albicans. FIG. 5 shows that α-MSH(1-13) (SEQ ID NO: 3) and (11-13) (SEQ ID NO: 1) enhanced cAMP content in the yeast. FIG. 6 shows the increase was of the same order of magnitude as that induced by equimolar forskolin, an adenylate cyclase activator. To determine whether increases in cAMP could be responsible for reduction in CFU, we tested the effects of forskolin on C. albicans viability. Results showed that $10^{-6}$M forskolin markedly inhibited C. albicans CFU relative to control (p<0.01). FIG. 6 demonstrates that the inhibitory effect was similar to that exerted by α-MSH (SEQ ID NO: 3).

The mechanism of action of natural antimicrobial agents is only partly understood. Most of these peptides, including the defensins, alter membrane permeability and impair internal homeostasis of the organism. The first contact is made between the cationic groups of the peptide and the negatively charged head of the target membrane. Then, the tertiary structure determines the mode of insertion of the peptide into membranes where they form ion channels or pores that disrupt cell integrity. It is known that cAMP-enhancing agents inhibit mRNA and protein synthesis in C. albicans. Bhattacharya, A., Datta, A., *Effect of Cyclic AMP on RNA and Protein Synthesis in C. albicans*, Biochem. Biophys. Res. Commun. 77: 1483–44 (1977).

These results suggest that the α-MSH peptides may exert their antifungal effect by increasing cAMP levels within the fungal cell. α-MSH(1-13) (SEQ ID NO: 3) and α-MSH(11-13) (SEQ ID NO: 1) both increased cAMP levels in *C. albicans*, with α-MSH(11-13) (SEQ ID NO: 1) having the larger effect of the two. The increase in cAMP caused by α-MSH(11-13) (SEQ ID NO: 1) was of the same order of magnitude as that caused by the adenylate cyclase activator forskolin. Forskolin was tested for its ability to inhibit *C. albicans* colony formation, and was shown to have an inhibitory effect between that of α-MSH(1-13) (SEQ ID NO: 3) and α-MSH(11-13) (SEQ ID NO: 1). The fact that forskolin inhibits fungal colony formation at a level similar to that of the α-MSH peptides, coupled with the finding that the α-MSH peptides increase cellular cAMP levels in a manner similar to forskolin, suggests that increased cAMP levels might be one mechanism by which α-MSH (SEQ ID NO: 3) exerts its antifungal effects. cAMP is formed via a G protein mediated pathway. G proteins are activated when a signaling molecule binds to a cell surface receptor, triggering a conformational change in the receptor. This conformational change causes the α subunit of the G protein to release GDP and bind GTP, forming the α-GTP subunit that activates adenylate cyclase. Adenylate cyclase then converts ATP to cAMP, which activates enzymes such as protein kinase A and causes the phosphorylation of a variety of downstream targets. It is believed that α-MSH (SEQ ID NO: 3) exerts its effects by binding to cell surface receptors that activate G proteins, or at any other step along the G protein pathway. Agents that increase adenylate cyclase activity and boost cellular cAMP levels have been shown to inhibit both mRNA synthesis and protein translation in *C. albicans* by phosphorylating downstream targets.

EXAMPLE 5

Example 5 suggests that systemic or topically administered α-MSH may be useful in reducing the inflammation associated with sinusitis. Example 5 further suggests that such applications of α-MSH (SEQ ID NO: 3) would be clinically therapeutic for the treatment of sinusitis. The anti-inflammatory activity of the tripeptide was demonstrated through the use of an anima model developed by Sparrow and Wilhelm (1957), J. Physiol., 137:51–65. This model relies on the principal that localized, subcutaneous injections of histamine will result in a localized increase in capillary permeability. When the test animal has been pre-treated with blue dye intravenously, the localized histamine injections will elicit blue-colored "weals" around the injection site. Thus, by preadministration of an effective anti-inflammatory agent the blue color of the histamine-induced weals will be much less pronounced, with the amount of color reduction being dependent on the relative amount and/or potency of the anti-inflammatory agent used.

Non-moulting New Zealand white rabbits were used for the Sparrow/Wilhelm assay. The skin of the rabbits back was closely clipped 1–2 days previous to the experiment, but not depilated, and the rabbits were kept warm until tested. Various amounts of the protected tripeptide Ac-Lys-Pro-Val-NH$_2$ (SEQ ID NO: 1) were injected intravenously into an ear vein approximately 15 minutes prior to intravenous injection of blue dye. Control rabbits received sham injections. Fifteen minutes following injection of the agent or sham, the rabbits received approximately 30 mg/kg of Pontamine blue dye as a 2.5% solution in 0.45% saline, into an exposed vein. Immediately following dye injections, histamine was injected intradermally in a 0.10 ml volume (1.25 mg histamine 0.1 ml volume) at several sites on each side of the spine. In all, one vertical row of six injections were made on each side of the spine. The relative intensity of the resultant blue weals were scored by an independent observer 30 minutes after histamine injection. The results are displayed in Table I below.

TABLE I

Anti-inflammatory Activity of the Tripeptide (SEQ ID NO: 1)

| No Animals Tested | (SEQ ID NO: 1) Tripeptide Dose + | Result |
| --- | --- | --- |
| 3 (2E, 1C) | 5 | E lighter than C |
| 2 (1E, 1C) | 10 | E lighter than C |
| 2 (1E, 1C) | 5 | E lighter than C |
| 2 (1E, 1C) | 1.25 | E lighter than C |
| 2 (1E, 1C) | 0.625 | No difference observed |

*E = experimental; C = control
+ Dosages in ug of protected tripeptide per kg body weight, administered intravenously.

As will be appreciated from the results displayed in Table I, intravenous doses down to 1.25 ug tripeptide (SEQ ID NO: 1) per kg body weight resulted in an appreciable reduction in histamine-induced blue weal formation and is thus indicative of an effective anti-inflammatory action. At doses of 5 and 10 ug/kg, the observed response was even more pronounced. Also as will be appreciated, the anti-inflammatory effect of the tripeptide is observed at relatively lower doses as compared to its anti-pyretic effect.

These results show that a peptide containing the KPV (SEQ ID NO: 1) amino acid sequence of α-MSH (SEQ ID NO: 3) has anti-inflammatory properties. Rabbits injected with histamine after injection of a blue marking dye will exhibit blue weal formation around the injection site. This occurs because histamine increases blood vessel permeability, allowing the dye to seep into the injection area. When the rabbits were pre-injected with as little as 1.25 µg/kg body weight of a protected KPV (SEQ ID NO: 1) tripeptide, the histamine-induced weal exhibited a substantially less intense blue color. This suggests that the KPV (SEQ ID NO: 1) tripeptide is interfering with the ability of histamine to increase blood vessel permeability. Histamine plays a central role in the inflammation reaction by dilating blood vessels, increasing vessel permeability, and increasing blood flow. Histamine also triggers the release of cytokines by leukocytes, which further increases the inflammation reaction. The ability of the KPV tripeptide (SEQ ID NO: 1) to block histamine function suggests that peptides containing the α-MSH KPV (SEQ ID NO: 1) amino acid sequence could serve as potent anti-inflammatory agents.

EXAMPLE 6

Example 6 still further suggests that the anti-inflammatory properties of α-MSH (SEQ ID NO: 3) may be clinically therapeutic for the treatment of sinusitis and may serve as substitute for corticosteriod based treatment regimens. A second in vivo bioassay for anti-inflammatory activity was conducted in which the action of the tripeptide (SEQ ID NO: 1) was compared to that of hydrocortisone. In this assay, the two agents were given at similar doses and tested for their independent ability to inhibit carrageenan-induced swelling in rat paws. This assay, the rat paw edema test, was conducted generally as it is typically performed in the art, for example, as described by Winter et al. (1962), Proc. Soc. Exp. Biol. Med., 111:544 or in U.S. Pat. No. 4,150,137.

Briefly, the assay was performed as follows. Each of twenty-four male Sprague-Dawley rats was assigned to one of four groups: Tripeptide treatment and controls (matched according to body weight and initial paw volume), hydrocortisone treatment and matched controls. The volume of the right rear paw of the test and control animals was determined using standard procedures and a mercury displacement volumetric technique. An intraperitoneal injection of the tripeptide (Ac-Lys-Pro-Val-NH$_2$, (SEQ ID NO: 1) 100 mg/kg, N=6), of hydrocortisone (100 mg/kg, N=6), or saline (matched volume, N=12) was given to each rat. One hour later 0.5 ml of 1% lambda carrageenan in saline solution was injected into the right rear paw of the animals and the paw volume was again recorded (baseline measure). For comparison of the effects of the two treatments, paw volume of experimental animals measured at hourly intervals was expressed as a percentage of the volume change of their respective matched controls.

Figure 7:
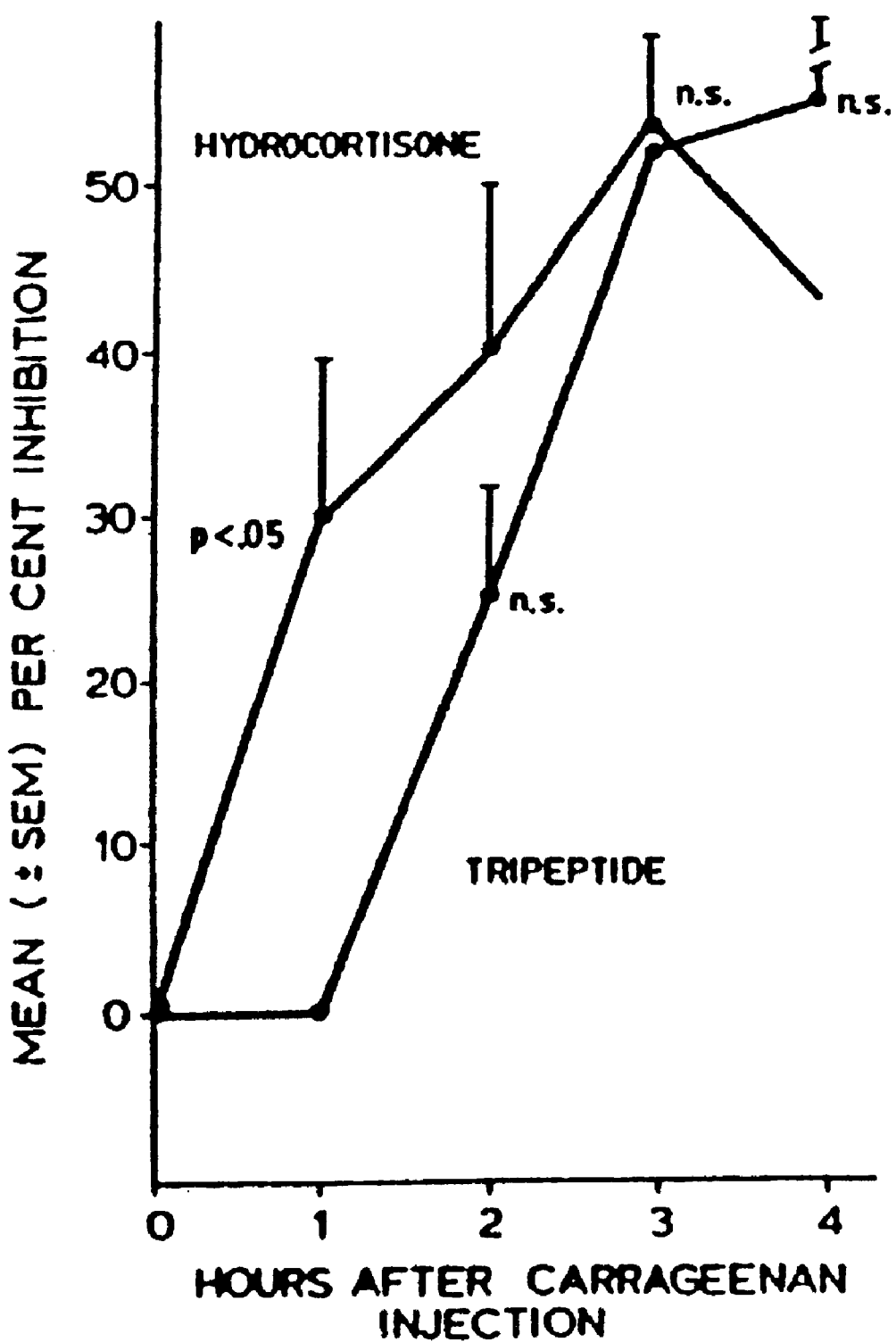
FIG. 7 illustrates the anti-inflammatory effects α-MSH (11-13) (SEQ ID NO: 3) relative to hydrocortisone on edema caused by injection of cargeenan. Scores are mean±SEM differences from baseline measures for control and peptide treatments.

The results of this experiment are shown in FIG. 7. As will be appreciated from this data, except for the first hour when hydrocortisone markedly inhibited swelling (p<0.05, Mann-Whitney test), there was no significant difference in the inhibition of paw edema caused by the tripeptide and hydrocortisone (p<0.20).

These results show that a peptide containing the KPV (SEQ ID NO: 1) amino acid sequence of α-MSH (SEQ ID NO: 3) could serve as a potential replacement for corticosteroids in the treatment of inflammation. α-MSH(11-13) (SEQ ID NO: 1) was compared to hydrocortisone for its ability to prevent carrageenan-induced rat paw inflammation. The development of swelling after carrageenan injection is a biphasic event. The first phase, occurring approximately 1 hour after injection, is attributed to the release of histamine and serotonin. The second phase is attributed to the release of prostaglandin-like substances, and is sensitive to both steroidal and non-steroidal anti-inflammatory agents. Prostaglandins are produced from arachidonic acid by cyclooxygenase, and like histamine they serve to increase blood vessel permeability. During the first hour after carrageenan injections, hydrocortisone caused approximately a 30% decrease in paw inflammation, while no such reduction was observed in the presence of α-MSH(11-13) (SEQ ID NO: 1). Between 1 and 4 hours, however, α-MSH (11-13) (SEQ ID NO: 1) and hydrocortisone exhibited nearly identical anti-inflammatory activity. Corticosteroids such as hydrocortisone inhibit inflammation by preventing the release of arachidonic acid from phospholipids, which in turn inhibits the formation of prostaglandins. While example 5 suggested that the α-MSH tripeptide (SEQ ID NO: 1) inhibits inflammation by blocking histamine function, example 6 suggests that α-MSH (SEQ ID NO: 3) may also inhibit inflammation via a mechanism similar to that of the corticosteroids. It is also believed that α-MSH (SEQ ID NO: 3) serves to inhibit inflammation by increasing the formation of endogenous corticosteroids. These substances are up-regulated by ACTH (SEQ ID NO: 9), which like α-MSH (SEQ ID NO: 3) is a melanocortin peptide. Regardless of the exact mechanism of α-MSH (SEQ ID NO: 3) anti-inflammatory activity, these results suggest that peptides containing the C-terminal α-MSH amino acid sequence KPV (SEQ ID NO: 1) have potential therapeutic utility in the treatment of inflammation, particularly inflammation tied to sinusitis.

EXAMPLE 7

Example 7 suggests that α-MSH (SEQ ID NO: 3) and its derivatives may be employed in general to reduce inflammation and in particular may be employed to reduce inflammation associated with sinusitis. Hiltz, M. E., Catania, A., Lipton, J. M., *Anti-Inflammatory Activity of aα-MSH (11-13) Analogs: Influence of Alteration in Stereochemistry*, 12 Peptides 767 (1981). More particularly Example 7 suggests that the COOH-terminal tripeptide of α-MSH has potent anti-inflammatory properties and further suggest that alterations in amino acid chirality tripeptide (SEQ ID NO: 1) can markedly affect the peptides α-MSH (SEQ ID NO: 3) anti-inflammatory properties. Female BALB/C mice (Simonsen Laboratories), 7 weeks old, were housed at 23–25° C. in groups of no more than 5 per cage [28 cm (L)×18 cm (W)×13 cm (H)]. They were allowed to acclimatize to standard lighting and temperature conditions for at least 1 week, with food and water available ad lib, before the experiment began. Five to ten animals were randomly assigned to each treatment group each test day, and all experiments were repeated at least twice to confirm reproducibility. To reduce error due to slight differences in responses to the irritant of animals from different shipments, tests of each agent were performed as separate experiments in which experimental and control animals were drawn from the same shipment.

In the experiments each animal was anesthetized with 1 mg of pentobarbital sodium solution (50 mg/kg, Nembutal, Abbott Laboratories, Abbott park, Ill.). Baseline ear thickness was measured for both ears with a spring-loaded micrometer (Swiss Precision Instruments, Los Angeles, Calif.). Ear thickness was expressed in units of $10^{-3}$ cm; the average thickness of unstimulated ears was approximately 25–30×$10^{-3}$ cm. After baseline measurements were taken, one of six solutions was injected IP. Control animals received 0.2 ml of sterile saline, and experimental animals received Ac-α-MSH(11-13)-NH$_2$ (SEQ ID NO: 1), i.e., Ac-Lys-Pro-Val-NH$_2$) (SEQ ID NO: 1) Ac[D-Lys$^{11}$]α-MSH (11-13)-NH$_2$ (SEQ ID NO: 5), Ac[D-Pro$^{12}$]α-MSH (11-13)-NH$_2$ (SEQ ID NO: 6), Ac[D-Val$^{13}$]α-MSH(11-13-NH$_2$ (SEQ ID NO: 7), or Ac-[D-Lys$^{11}$, D-Val$^{13}$]α-MSH(11-13)-NH$_2$ (SEQ ID NO: 8) in the same volume of saline. All of the peptides were custom synthesized by Peninsula Laboratories (Belmont, Calif.) and were determined to be both pure by HPLC and to possess the expected amino acid analytical composition. The doses of the tripeptides were 10 μg (2.6×$10^{-8}$ M), 20 μg (5.2×$10^{-8}$ M), 40 μg (1.04×$10^{-7}$ M), and 80 μg (2.08×$10^{-7}$ M). Immediately after saline or α-MSH injection, a micropipette was used to coat both sides of each ear with 10 μl (40 μl per mouse) of a 0.5% picryl chloride (Polysciences, Warrington, Pa.) solution in acetone.

Ear thickness was remeasured 3 and 6 h after picryl chloride application. Swelling was determined by subtracting baseline thickness from the measurements for each ear at 3 and 6 h. The differences for both ears were then averaged for the final analysis. On rare occasions when swelling did not occur in the control animals, the data for that day were considered invalid and were not used in the final analysis.

Repeated-measure ANOVA techniques were used to determine if there was an overall difference among group data for each peptide tested in separate experiments. In those cases in which the ANOVA yielded significant results, Dunnett's test was then used to compare the effects of peptide doses with control (saline) data for each of the two time periods, 3 and 6 h.

Figure 8:
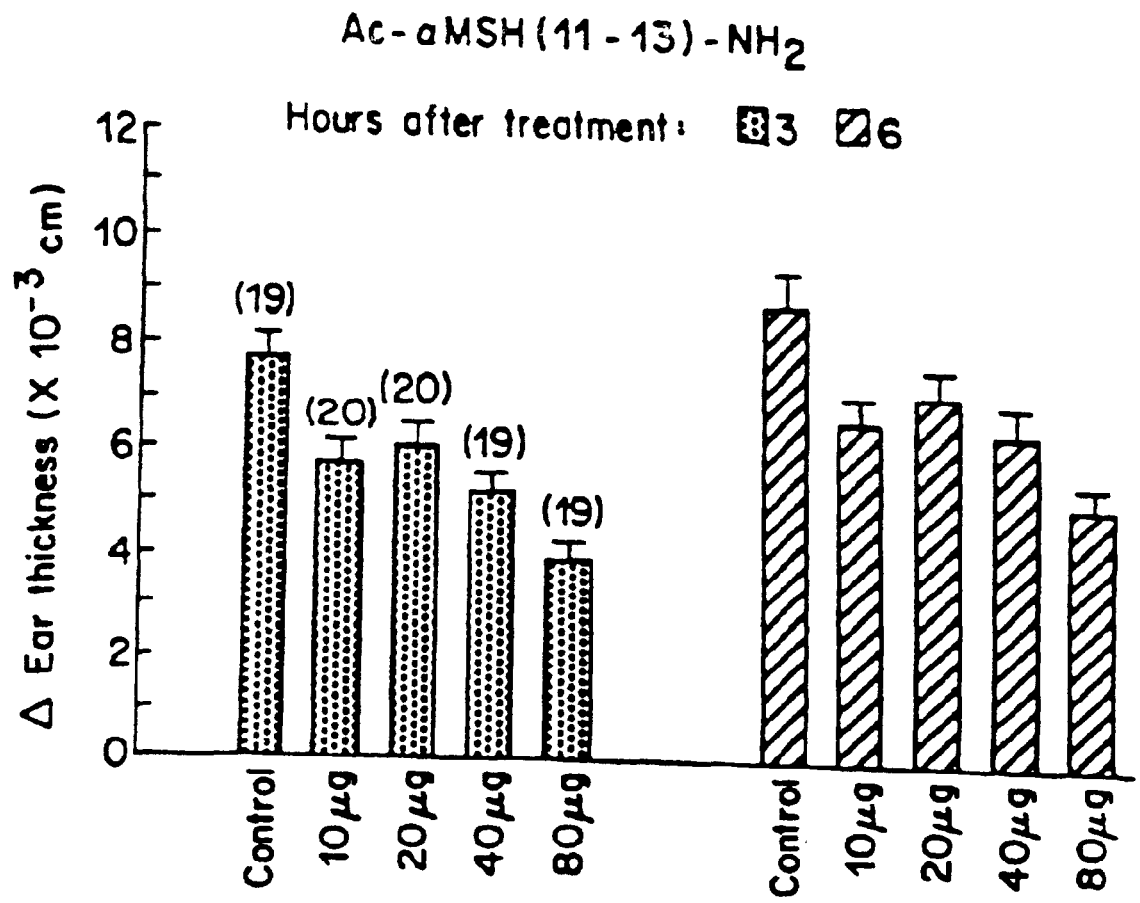
FIG. 8 illustrates inhibition by α-MSH(11-13) (SEQ ID NO: 1) of inflammation induced in the ear by picryl chloride application. Scores are mean±SEM differences from baseline measures for control and peptide treatments. Number of animals shown in parentheses.

FIG. 8 illustrates inhibition by α-MSH(11-13) (SEQ ID NO: 1) of inflammation induced in the ear of a mouse induced by picryl chloride application. Ac-α-MSH(11-13)-NH$_2$ (SEQ ID NO: 1) inhibited acute inflammation. The ANOVA showed a highly significant dose effect, $F(4,92)$= 9.35, p<0.0001. There was also a significant time effect, F(1,92)=40.8, p<0.001, but no significant interaction. The average swelling in the controls was significantly greater than in any of the peptide treatment groups at both 3 and 6 h (p<0.05, Dunnett's test, two-tail).

Figure 9:
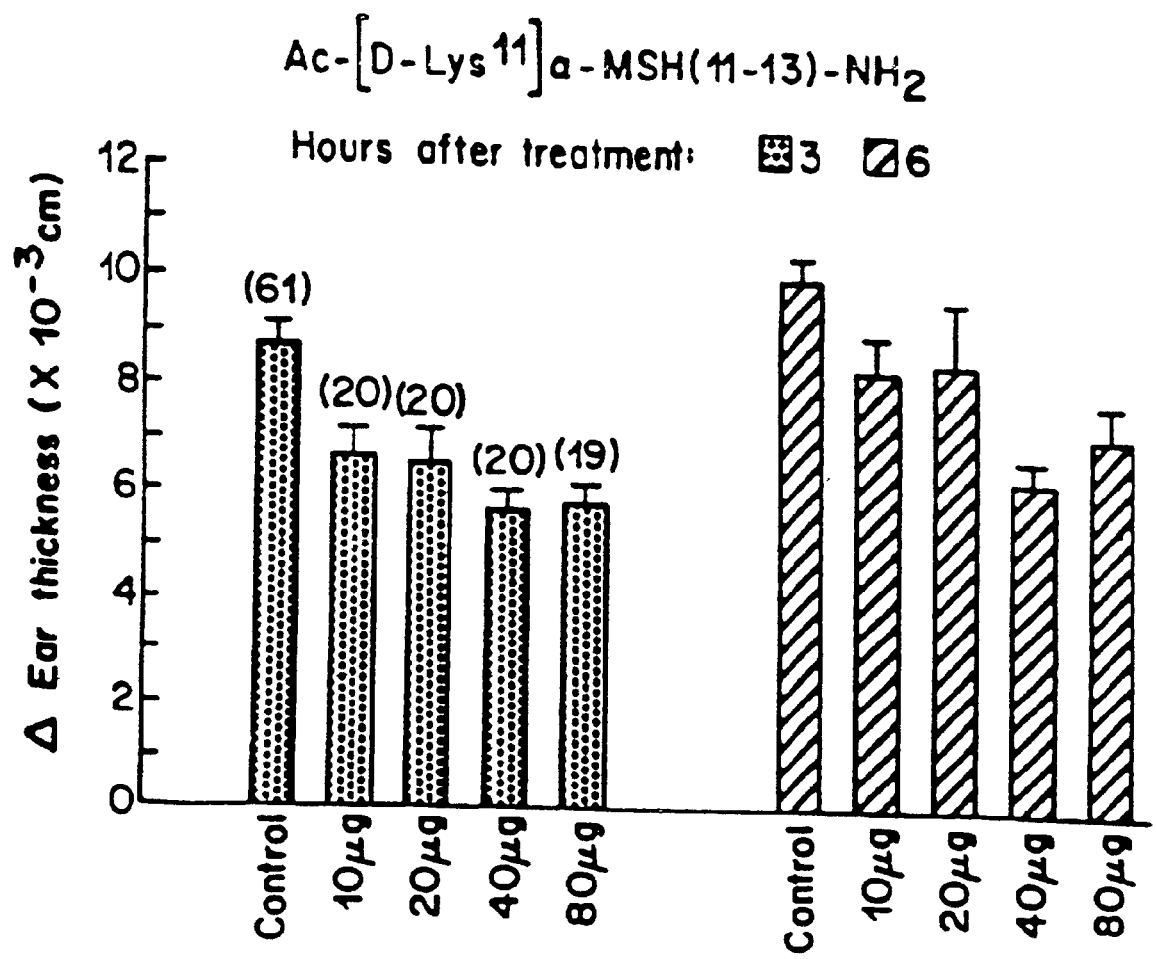
FIG. 9 illustrates inhibition of inflammation by Ac-[D-Lys$^{11}$]α-MSH(11-13)-NH$_2$ (SEQ ID NO: 5). Scores are mean±SEM differences from baseline measures for control and peptide treatments. Number of animals shown in parentheses.
Figure 10:
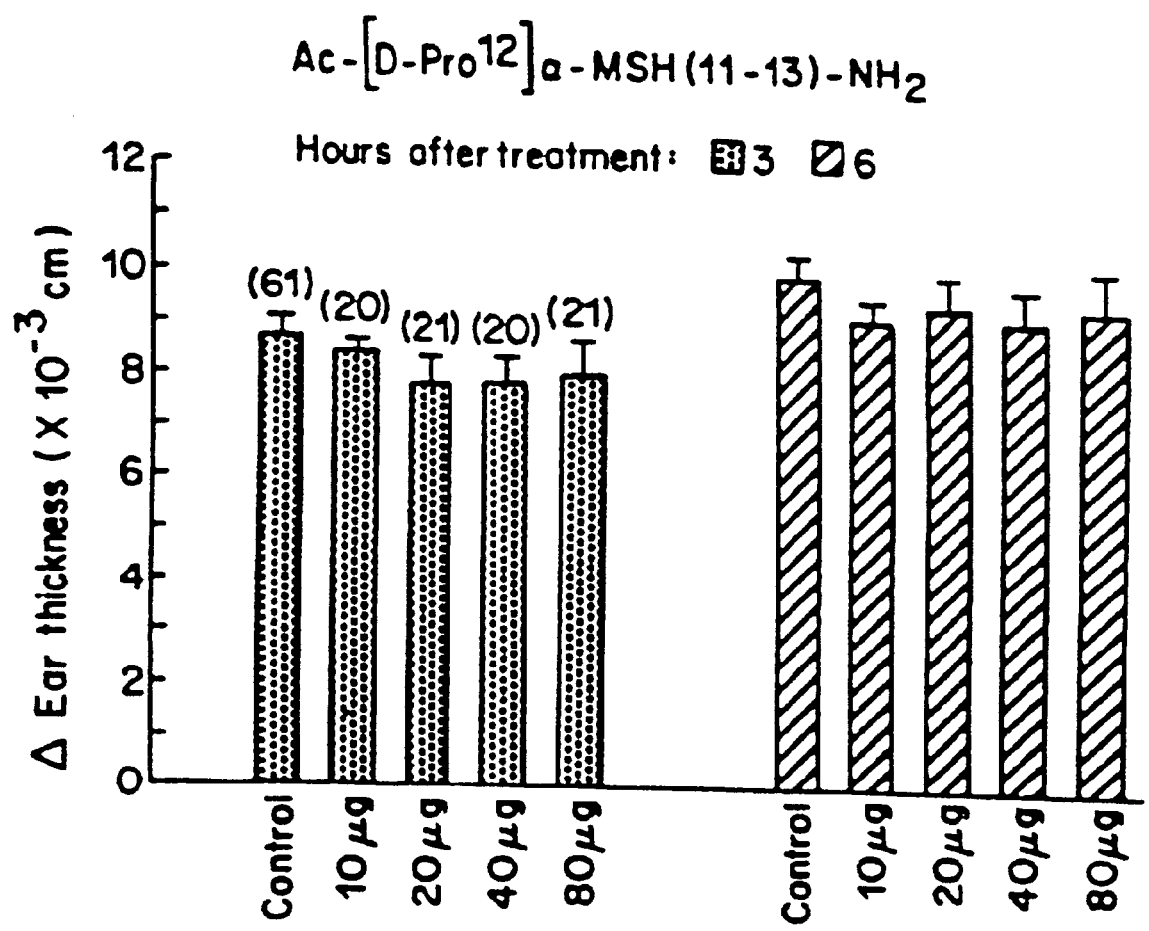
FIG. 10 illustrates the lack of inflammation by Ac-[D-Pro$^{12}$]α-MSH(11-13)-NH$_2$ (SEQ ID NO: 6). Scores are mean±SEM differences from baseline measures for control and peptide treatments. Number of animals shown in parentheses.
Figure 11:
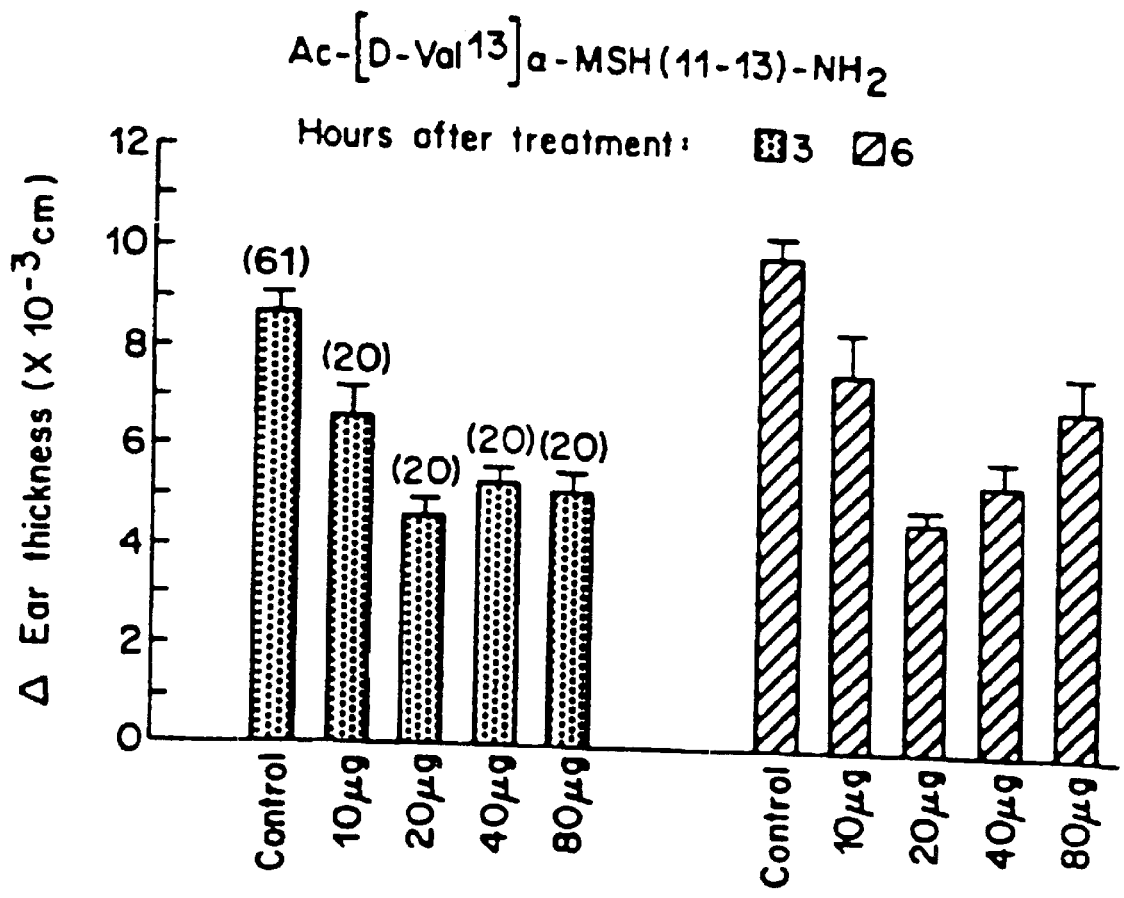
FIG. 11 illustrates the inhibition of inflammation by Ac-[D-Val$^{13}$]α-MSH(11-13)-NH$_2$ (SEQ ID NO: 7). Scores are mean±SEM differences from baseline measures for control and peptide treatments. Number of animals shown in parentheses.

FIG. 9 illustrates that Ac[D-Lys$^{11}$]α-MSH(11-13)-NH$_2$ (SEQ ID NO: 5) likewise significantly reduced inflammation [F(4,135)=7.83 p<0.0001] in the ear of a mouse induced by picryl chloride application. Ear swelling after all doses of peptide was less than control (p<0.05). There was a significant time effect, F(1,135)=43.8, p<0.001, but no significant dose-time interaction. FIG. 10 illustrates that Ac[D-Pro$^{12}$]α-MSH(11-13)-NH$^2$ (SEQ ID NO: 6) had no significant effect on inflammation [F(4,139)=0.62, p>0.65]. By contrast, FIG. 11 illustrates that Ac[D-Val$^{13}$]α-MSH (11-13)-NH$_2$ (SEQ ID NO: 7) had a marked inhibitory influence [F(4,136)=19.6 p<0.001]. There was a significant time effect in the Ac[D-Val$^{13}$] experiment, F(4,138)=3.96, p<0.005, likely due to increases over time for the control, 10 and 80 μg groups and little change for the 20 and 40 μg groups. Dunnett's test applied to control and treatment data for the 3- and 6-h time periods indicated that the control swelling was significantly greater than in the peptide treatment groups (p<0.01).

Figure 12:
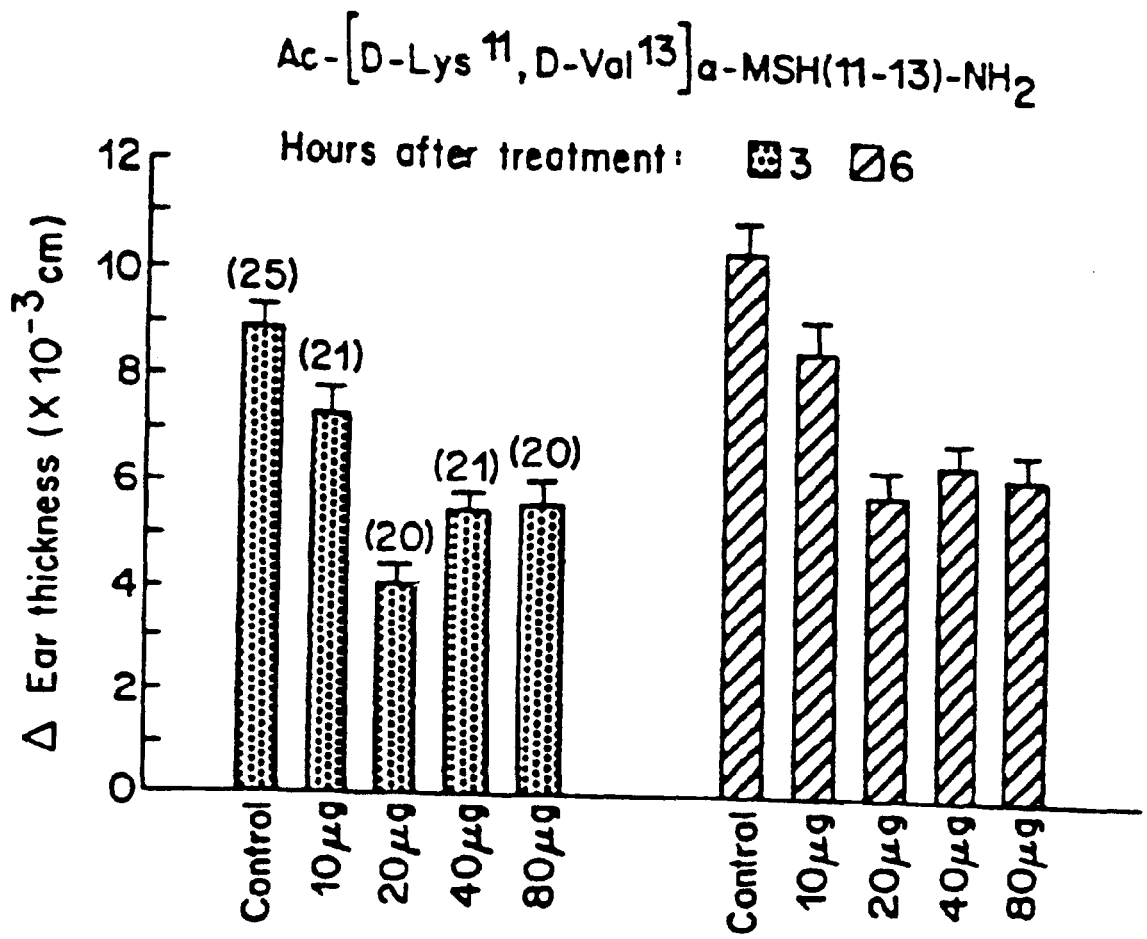
FIG. 12 illustrates inhibition of inflammation by Ac-[D-Lys$^{11}$, D-Val$^{13}$]α-MSH(11-13)-NH$_2$ (SEQ ID NO: 8). Scores are mean±SEM differences from baseline measures for control and peptide treatments. Number of animals shown in parentheses.

As FIG. 12 illustrates, Ac-[D-Lys$^{11}$, D-Val$^{13}$]α-MSH(11-13)-NH$_2$ (SEQ ID NO: 8) showed a significant overall reduction in inflammation [F(4,102)=19.8, p<0.0001], and a significant time effect, F(1,102)=73.2 p<0.0001, but no significant interaction. Treatment means were all significantly (p<0.01) less than control values for both the 3- and 6-h measurements.

As is shown in Table 2, the results of the experiments were converted to percent inhibition of swelling for comparisons of the effectiveness of the peptide conformations. The two peptides with D-Val$^{13}$ conformation induced more consistent, large anti-inflammatory effects at 3 and 6 h than did the other tripeptides. Although in these experiments, the well-known bell-shaped influence of peptides complicated the comparisons, the D-Val$^{13}$ tripeptides were generally more potent and their effects were sustained in the 6-h measurement. D-Lys$^{11}$ substitution did not increase the potency or duration of anti-inflammatory activity and the strong action of the largest does of Ac-α-MSH(11-13)-NH$^2$ (SEQ ID NO: 1) suggests that its actions rank roughly third among those recorded. The lack of significant effect on inflammation of the Ac[D-Pro$^{12}$]α-MSH(11-13)-NH$_2$ (SEQ ID NO: 6) indicates that the L-Pro configuration is likely central to the anti-inflammatory activities of the molecule.

TABLE 2

|  | % Inhibition | | Amino Acid | |
| --- | --- | --- | --- | --- |
|  | 3 h | 6 h | Analysis | % Purity |
| Ac-α-MSH(11-13)-NH$_2$ |  |  | K(0.99), P(1.01), V(0.94) | >99 |
| 10 μg | 26 | 25 |  |  |
| 20 μg | 21 | 19 |  |  |
| 40 μg | 33 | 26 |  |  |
| 80 μg | 50 | 42 |  |  |
| Ac-[D-Lys$^{11}$]α-MSH(11-13)-NH$_2$ |  |  | K(0.97), P(1.03), V(0.94) | >93 |
| 10 μg | 23 | 17 |  |  |
| 20 μg | 25 | 16 |  |  |
| 40 μg | 35 | 37 |  |  |
| 80 μg | 34 | 29 |  |  |

TABLE 2-continued

|  | % Inhibition | | Amino Acid | |
| --- | --- | --- | --- | --- |
|  | 3 h | 6 h | Analysis | % Purity |
| Ac-[D-Pro$^{12}$]α-MSH(11-13)-NH$_2$ |  |  | K(0.99), P(1.01), V(0.97) | >93 |
| 10 μg | 4 | 8 |  |  |
| 20 μg | 11 | 5 |  |  |
| 40 μg | 10 | 8 |  |  |
| 80 μg | 8 | 6 |  |  |
| Ac-[D-Pro$^{13}$]α-MSH(11-13)-NH$_2$ |  |  | K(0.99), P(1.01), V(0.97) | >96 |
| 10 μg | 24 | 23 |  |  |
| 20 μg | 48 | 54 |  |  |
| 40 μg | 39 | 45 |  |  |
| 80 μg | 41 | 29 |  |  |
| Ac-[D-Lys$^{11}$, D-Val$^{13}$]α-MSH(11-13)-NH$_2$ |  |  | K(1.04), P(0.91), V(1.05) | >99 |
| 10 μg | 22 | 22 |  |  |
| 20 μg | 55 | 46 |  |  |
| 40 μg | 42 | 41 |  |  |
| 80 μg | 40 | 44 |  |  |

Altering the stereochemical make-up of the tripeptide via D-substitution had two major effects: increased potency in the case of Ac[D-Val$^{13}$], α-MSH(11-13)-NH$_2$ (SEQ ID NO: 7) and Ac-[D-Lys$^{11}$, D-Val$^{13}$]α-MSH(11-13)-NH$_2$ (SEQ ID NO: 8) and reduced the anti-inflammatory activity in Ac[D-Pro$^{12}$]α-MSH(11-13)-NH$_2$ (SEQ ID NO: 6).

These results again show the ability of the α-MSH(11-13) (SEQ ID NO: 1) tripeptide to inhibit inflammation, as well as illustrating the importance of chirality to the effectiveness of the peptide. α-MSH(11-13) reduced mouse ear swelling in the presence of the skin irritant picryl chloride at doses as low as 2.6×.10$^{-8}$ M. At the highest α-MSH(11-13) (SEQ ID NO: 1) dosage, 2.08×.10$^{-7}$ M, inflammation was reduced by 50% 3 hours after picryl chloride treatment. The anti-inflammatory effect of α-MSH(11-13) (SEQ ID NO: 1) was reduced after 6 hours, but there was still significantly less ear swelling than in the control mice. When the chirality of the amino acids making up the α-MSH tripeptide was switched from the L configuration to the D configuration, there was a direct effect on peptide activity. Switching the proline residue to the D-form caused the most marked change, completely destroying the ability of the tripeptide to inhibit inflammation. Switching the lysine residue to the D-form created a tripeptide that was similar to the L-form version in its ability to inhibit inflammation at low concentrations, but not as effective at higher concentrations or over longer time periods. Switching the valine residue to the D-form, either alone or in conjunction with the lysine residue, created a tripeptide that was more effective at inhibiting inflammation than the standard L-form version. This peptide inhibited inflammation at lower concentrations than the D-form peptide, and was effective over a longer time period and suggests that the use of such peptides might serve to prevent unwanted side effects in a therapeutic setting by making it less likely that the peptide will interact with other compounds.

EXAMPLE 8

Example 8 suggests that α-MSH reduces inflammation through both centrally and peripherally mediated mechanisms and accordingly, systemic or topical administration of α-MSH may be therapeutically effective in the treatment of sinusitis. See Macaluso, A., McCoy, D., Ceriani, G., Watanabe, T., Biltz, J., Catania, A., and Lipton, J. M., *Anti-inflammatory Influences of a-MSH Molecules: Central*

*Neurogenic and Peripheral Actions,* 14(4), J. of Neuroscience 2377–2382 (1994). Female BALB/c mice (Simonsen Laboratories, Gilroy, Calif.), 7–8 weeks old, were housed at 23–25° C. in groups not exceeding five animals per cage [28 cm (L)×18 cm (W)×13 cm (H)]. Before the experiments they were acclimatized for not less than 1 week before experimentation to standard lighting and temperature conditions with food and water freely available.

Mice were anesthetized with 10% pentobarbital sodium solution (1 mg/mouse, 50 mg/ml, Nembutal sodium solution; Abbott Laboratories, North Chicago, Ill.). Baseline ear thickness measurements were taken with a spring-loaded micrometer (Swiss Precision Instruments, Los Angeles, Calif.). Ear thickness was expressed in centimeters and was measured at least twice at each time point. The average thickness of unstimulated ears was 26.82 cm$^{-3}$. Inflammation was induced by injecting 20 µl of recombinant human IL-1β (1500 U; Genzyme, Cambridge, Mass.) directly into the skin (intradermally) of one ear of each mouse using a 28 gauge needle (Hiltz et al., 1992). Measures of ear thickness were repeated 4 and 6 hr later, while the mice were under sodium pentobarbital anesthesia. Edema was assessed by subtracting baseline measures from 4 and 6 hr readings for each animal. α-MSH(1-13) (SEQ ID NO: 3) (1663.9 gm/mol; Peninsula Laboratories, Belmont, Calif.) or α-MSH(11-13) (SEQ ID NO: 1) (383.48 gm/mol; Peninsula Laboratories) dissolved in saline was injected intracerebroventricularly (20 µl) using procedures described previously (Lipton et al., 1991; Lipton and Catania, 1993).

Several agents were administered at the time of ear challenge to pharmacologically block certain receptors: atropine (Sigma Chemical Co.; 150 µg i.p.), a muscarinic receptor blocker that acts on autonomic end-organ receptors, was chosen because of links between inflammation and modulation of pain and the finding that muscarinic antagonists increase pain threshold (Hartvig et al., 1989); phentolamine (Sigma; 150 µg i.p.) an agent that competes for occupancy of α-adrenergic receptors; propranolol (Sigma; 150 µg, i.p.; 30 µg, i.c.v.), a nonspecific competitive antagonist for β-adrenergic receptors. After positive effects were observed with propranolol, selective antagonists of β-adrenergic receptors were tested; atenolol (Sigma; 150 µg, i.p.), a β-adrenergic receptor antagonist; butoxamnine (Sigma; 150 µg, i.p.), a β$_2$-adrenergic receptor blocker.

Because surgical dissection of trigeminal structures that innervate the ear of the mouse is very difficult, tests to learn whether descending neural pathways are essential to the anti-inflammatory activity of centrally administered α-MSH peptides were performed in mice with inflammation induced in a hind paw. In these experiments, each animal was anesthetized with pentobarbital sodium solution as above. Baseline foot pad thickness of both hind paws was measured with a spring-loaded micrometer (Swiss Precision Instruments, Los Angeles, Calif.). Paw thickness was expressed in units of 10$^{-3}$ cm; average thickness of unstimulated paws was 171.5×10$^{-3}$ cm across shipments of animals. Kappa carrageenan (Sigma) dissolved in saline (0.05%, 20 µl) was injected (28 gauge allergy test syringe) into one footpad, and saline (20 µl) was injected into the other. For the analyses, the increase in thickness of the control saline-injected paw of each animal was subtracted from that of the carrageenan-injected paw, to eliminate the influence of mechanical injury and volume of the injected fluid. To be certain that mice with severed spinal cords can react to anti-inflammatory agents, prednisolone (2.5 mg/mouse i.p.) was administered to 10 mice with spinal transection and inflammation induced by carrageenan. Treatment with the locally acting steroid reduced swelling up to 29% (average, relative to saline controls) at 4.5 hr. after carrageenan. This finding indicates that spinal transection in these mice does not result in stasis of inflammation that is unalterable as a result of vasodilation, hypotension, or other hemodynamic changes.

Pilot studies indicated that interruption of the spinal cord of the mouse by surgical exposure, visualization, and severing with a scalpel blade resulted in marked bleeding, morbidity, and death in a substantial number of animals. However, a standardized crushing of lumbar vertebrae with a hemostat (Kelly) was effective in severing the cord; no deaths were caused by this treatment. In the experiments proper, all animals were tested after cord section when the anesthesia had worn off: none showed behavioral or motor responses to pinching of the hind feet with a hemostat; all had complete paralysis of the hind limbs. Data of animals that did not meet these criteria were excluded from the analyses. The experiments were limited to 4.5 hr to reduce problems of bowel and bladder dysfunction. Immediately after the 4.5 hr measurements all mice were killed with an overdose of sodium pentobarbital.

Because of the size of the experiments and the requirement for several shipments of animals over time, several experiments were performed, each with complete treatment and control groups drawn from the same shipment of mice. Omnibus analysis of variance techniques (Dynastat, Washington, D.C.) were used to test overall differences among group means. Tukey's protected t test was used to compare individual means. Probability values of <0.05 were considered significant.

Figure 13:
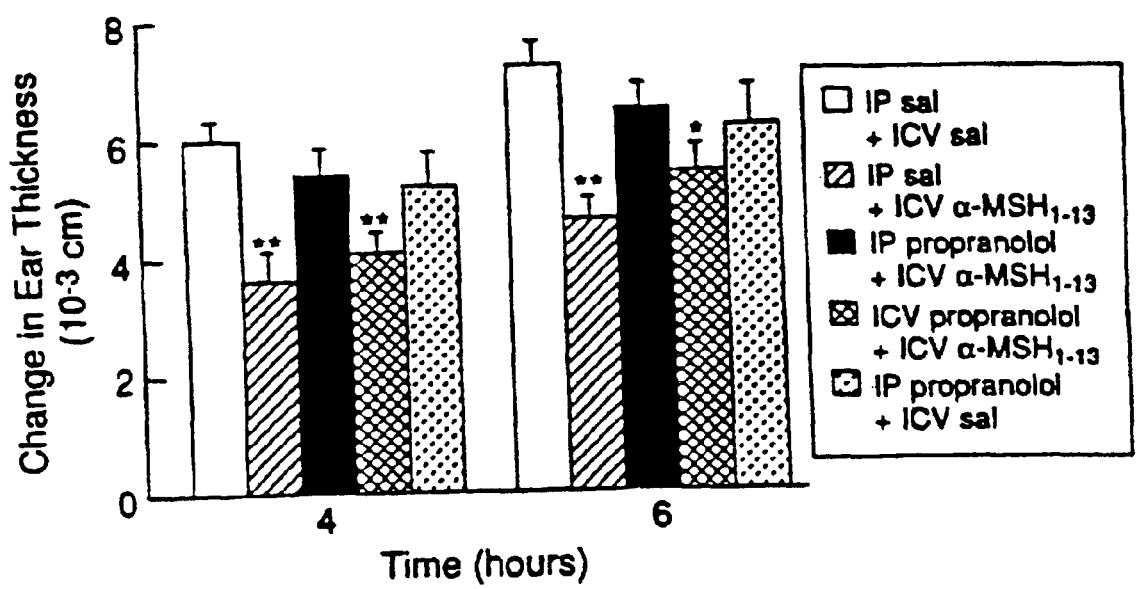
FIG. 13 illustrates the relative inhibition of α-MSH(11-13)'s (SEQ ID NO: 1) anti-inflammatory action on edema caused by intradermal injection of human recombitant 1L1β in the mouse ear. "IP" refers to intraperitonical injection 1 "Sal" refers to a saline solution. "ICV" refers to an intracerebroventricular injection.
Figure 14:
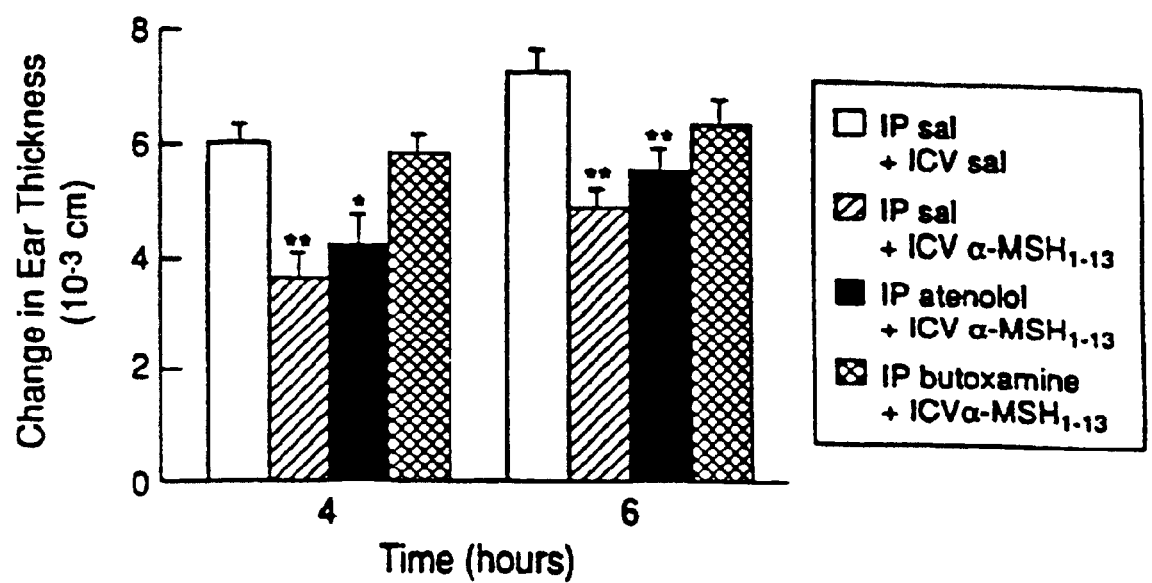
FIG. 14 illustrates the relative inhibition of the anti-inflammatory actions of centrally administered α-MSH(11-13) (SEQ ID NO: 1) by β$_2$-adregeneric antagonist butoxamine. Atenolol is a β$_1$-adrenergic antagonist.
Figure 15:
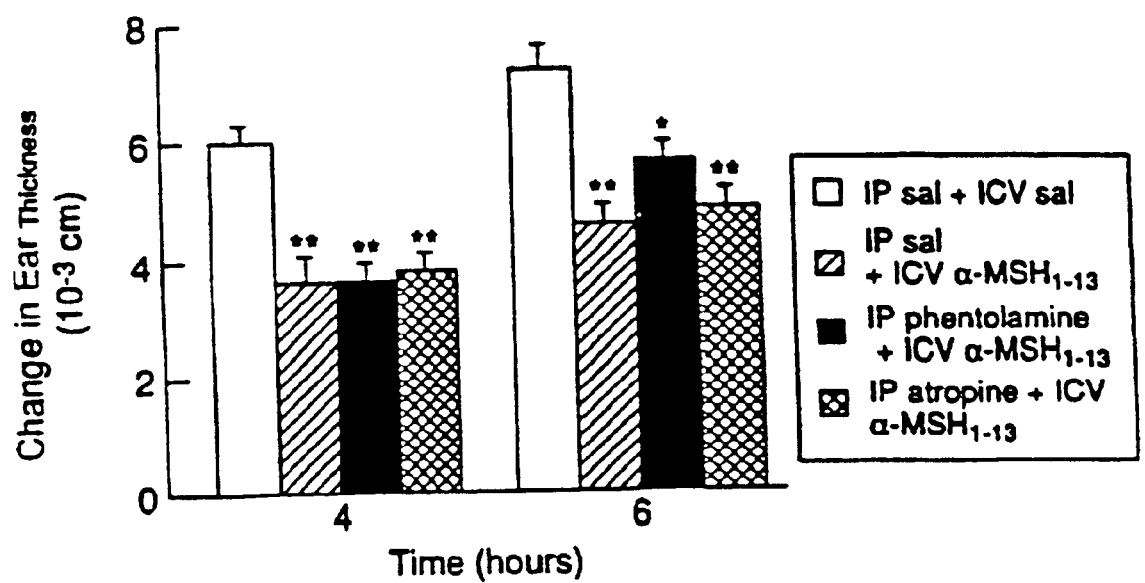
FIG. 15 illustrates the relative inhibition of the anti-inflammatory actions of centrally administered α-MSH(11-13) (SEQ ID NO: 1) in the presence of an α-receptor antagonist. Phentolamine is a cholinergic receptor antagonist.

In order to determine whether α-MSH anti-inflammatory properties are centrally or peripherally mediated, propranolol, a β-receptor blocker, was administered centrally and peripherally. As is shown in FIG. 13, when propranolol was injected centrally there was little effect on the anti-inflammatory influence of α-MSH(1-13) (SEQ ID NO: 3) (inhibition by α-MSH (SEQ ID NO: 3) was 36% and 32% at 4 hr and 6 hr respectively). By contrast when 300 µg of propranolol was administered intraperitoneally, the anti-inflammatory response of α-MSH was inhibited. This indicates that competitive binding of peripheral β-receptors inhibits the anti-inflammatory influence of centrally administered α-MSH. Subsequent tests determined the role of which β-adrenergic receptors were connected with the anti-inflammatory effect of centrally administered α-MSH. As is shown in FIG. 14, when atenolol, a β$_1$ adrenergic antagonist was injected IP, there was little inhibition of α-MSH(1-13)'s (SEQ ID NO: 3) anti-inflammatory activity. By contrast, when the β$_2$-receptor antagonist, butoxamine, was similarly administered, the α-MSH(1-13)'s (SEQ ID NO: 3) anti-inflammatory effects were significantly reduced. These results indicate that β$_2$-receptor activity in the periphery is essential to the anti-inflammatory action of α-MSH (SEQ ID NO: 3). As is shown in FIG. 15, blockade of α-adrenergic receptors with phentolamine, and cholinergic (muscarinic) receptors with atropine, did not alter the anti-inflammatory effect of α-MSH(1-13) (SEQ ID NO: 3).

Figure 16:
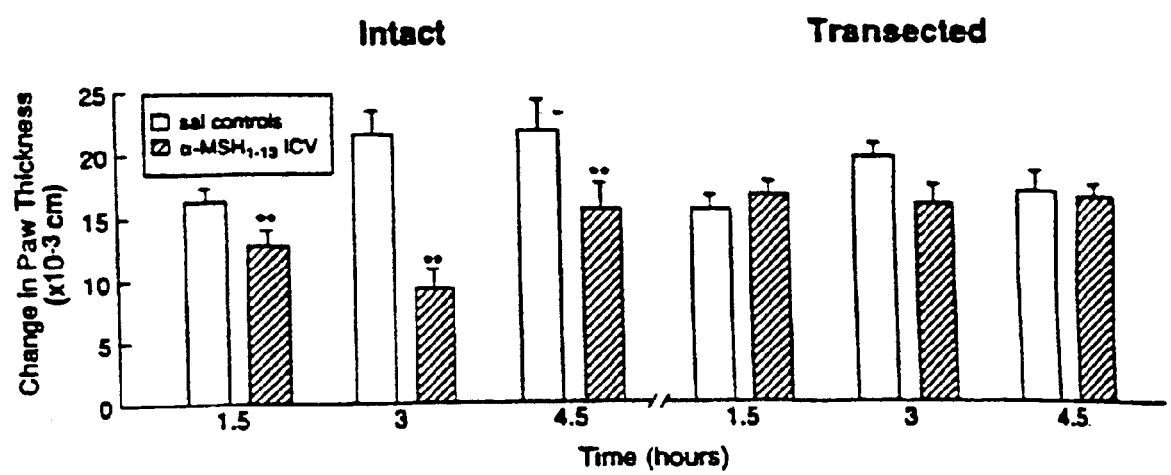
FIG. 16 illustrates the relative inhibition of the anti-inflammatory actions of centrally administered α-MSH(11-13) (SEQ ID NO: 1) as a function of time in spinal cord transected mice.
Figure 17:
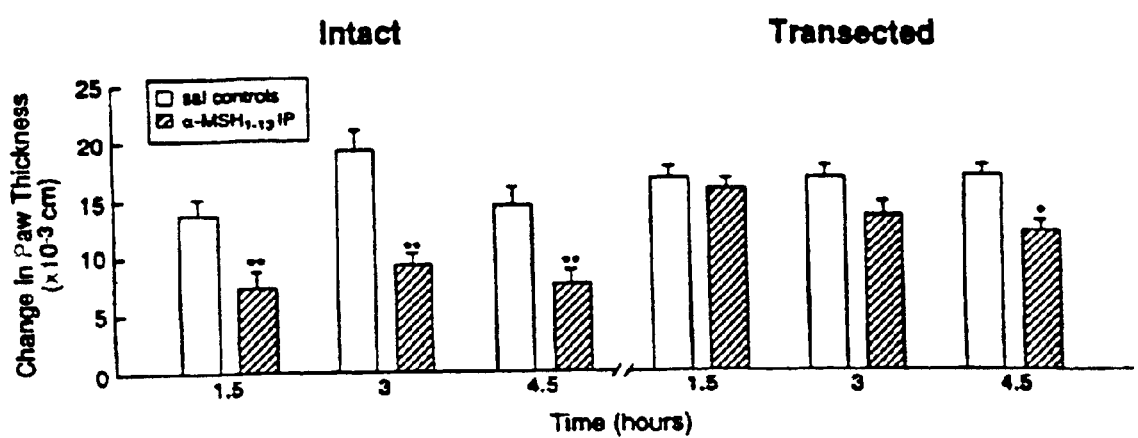
FIG. 17 illustrates the relative inhibition of the anti-inflammatory actions of systemically administered α-MSH (11-13) (SEQ ID NO: 1) as a function time in spinal cord transected mice.

As shown in FIG. 16, central administration of α-MSH (1-13) (SEQ ID NO: 3) in spinal cord intact mice markedly inhibited inflammation induced in the hind paw. The greatest effect was at 3 hr (57% inhibition); inhibition was less at 4.5 hr (29%). By contrast, spinal cord transection significantly reduced the anti-inflammatory effect of centrally administered α-MSH(1-13) (SEQ ID NO: 3). As is shown in FIG. 17, although transection of the spinal cord significantly reduced the early anti-inflammatory effect of α-MSH(1-13)

(SEQ ID NO: 3) given intraperitoneally, there was a significant, although smaller, inhibitory effect later in the period.

Figure 18:
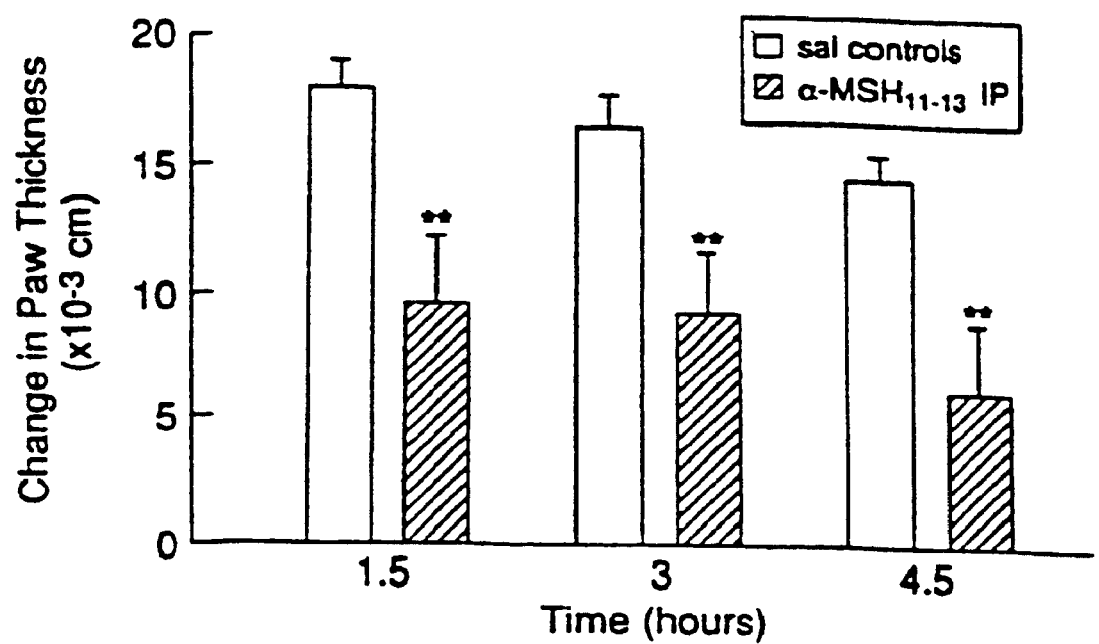
FIG. 18 illustrates the relative inhibition of the antinflammatory actions of systemically administered α-MSH(11-13) (SEQ ID NO: 1) as a function time in spinal cord transected mice.

To determine if the influence of systemically administered α-MSH requires it to act on the brain to induce descending inhibitory signals, α-MSH(1-13) (SEQ ID NO: 3) was administered IP to mice with spinal cord transection. FIG. 18 suggests that the tripeptide had a marked inhibitory effect on inflammation.

These results show that the α-MSH peptides reduce inflammation through both centrally and peripherally mediated mechanisms. The effect of intracerebroventricularly-injected α-MSH(1-13) (SEQ ID NO: 3) on IL-1β-induced mouse ear inflammation was tested in the presence of several receptor-blocking agents. When mice were centrally injected with propranolol, a β-receptor blocker, there was little change in the anti-inflammatory effects of α-MSH(1-13)(SEQ ID NO: 3). However, when propranolol was injected peripherally, there was a substantial decrease in the anti-inflammatory effectiveness of α-MSH(1-13) (SEQ ID NO: 3). Injection of the mice with an α-adrenergic receptor antagonist (phentolamine) or a cholinergic receptor antagonist (atropine) had no effect on α-MSH(1-13) (SEQ ID NO: 3) activity, regardless of whether these were injected centrally or peripherally. This suggests that centrally injected α-MSH(1-13) exerts its anti-inflammatory effects through a peripheral β-receptor pathway. To determine which β-receptors were involved, α-MSH(1-13) (SEQ ID NO: 3) activity was measured in the presence of either a $β_1$-adrenergic receptor antagonist (atenolol) or a $β_2$-receptor antagonist (butoxamine). Atenolol had little effect on the anti-inflammatory activity of α-MSH(1-13), (SEQ ID NO: 3), while butoxamine reduced this activity substantially. This suggests that it is the $β_2$ receptors of the peripheral nervous system that mediate the anti-inflammatory effect of α-MSH(1-13) (SEQ ID NO: 3).

The anti-inflammatory effect of α-MSH (SEQ ID NO: 3) was next measured in mice with transected spinal cords. Centrally injected α-MSH(1-13) (SEQ ID NO: 3) greatly reduced carrageenan-induced paw swelling in mice with intact spinal cords, but had no effect on paw swelling in transected mice. Peripherally injected α-MSH(1-13) (SEQ ID NO: 3), on the other hand, reduced swelling in both intact and transected mice, although the effect was not as marked in the transected mice and took longer to occur. Peripherally injected α-MSH(11-13) (SEQ ID NO: 1) was even more effective at reducing swelling in transected mice, displaying a level of inhibition similar to that seen in intact mice treated with α-MSH(1-13) (SEQ ID NO: 3). These results suggest that the α-MSH peptides do not have to act on the brain to produce descending inhibitory signals, meaning that either topical or systemic administration of α-MSH peptides should be effective in treating inflammation, especially inflammation related to sinusitis.

EXAMPLE 9

Example 9 suggests that the anti-inflammatory peptides of α-MSH (SEQ ID NO: 3) may be associated with reducing the cytokines connected to the inflammatory response including IL-6 and TNF-α and NO. See Delgado, R., Carlin, A., Alraghi, L., Demitri, M., Meda, L., Galimberti, D., Pierluigi, B., Lipton, J. M., Catania, A., *Melanocortin Peptides Inhibit Production of Proinflammatory Cytokines and Nitric Oxide by Activated Microglia,* 63 J. of Leukocyte Biol. 740 (1998). This further suggests the α-MSH may be the therapeutically effective, when administered topically or systemically for the treatment of sinusitis. The N9 clone of murine microglial cells was obtained by immortalization of embryonic brain cultures with the 3RV retrovirus carrying an activated v-myconcogene. N9 cells were cultured in T-75-$cm^2$ culture flasks (Coming, Cambridge, Mass.) and maintained at 37° C. in a humidified incubator under 5% $CO_2$ atmosphere in RPMI 1640 supplemented with 2 mM L-glutamine, 50 U/mL penicillin G, 50 μg/mL streptomycin sulfate (GIBCO-BBL, Paisley, UK), and 10% heat-inactivated fetal bovine serum (FBS, Hyclone Lab, Inc., Logan, Utah) until experiments were performed. Cells were used between the first and the tenth passage.

Sub-confluent microglial cells were washed twice with phosphate-buffered saline (PBS) and incubated with trypsin 0.025% and ethylenediaminetetraacetate (EDTA) 0.02% without calcium and magnesium for 3 min. at 37° C. to detach the cells from the culture flask. Cells were then resuspended in medium and incubated in 24-well tissue-culture plates at a concentration of $2×10^5$ cells/mL for 16 h in a humidified incubator (37° C., 5% $CO_2$). Growth medium was removed and cell monolayers were stimulated with 10 ng/mL lipopolysaccharide (LPS, from *Escherichia coli* 055:B5, Sigma Chemical Co., St. Louis, Mo.) plus 1 U/ml, murine IFN-γ (Sigma). To test effects of melanocortin peptides, concentrations (1, 10, 25, 50 and 100 μM) of α-MSH(1-13) (SEQ ID NO: 3), α-MSH(11-13) (SEQ ID NO: 1), and ACTH(1-24) (SEQ ID NO: 12) (Sigma) were dissolved in medium and added to wells 10 min before treatment with LPS+IFN-γ. Although production of TNF-α and NO was reduced to even much lower concentrations of the peptides, concentrations in the micromolar range had the most profound and consistent inhibitory effects. Although lower concentrations were more effective in previous research, we elected to use micromolar concentrations in the present studies because they were more effective for the experimental conditions (cell type, incubation period, concentration of the stimuli). Cell-free supernatants were harvested after 24 h incubation and assayed for TNF-α, IL-6 and $NO_2$. Viability of cells was assessed by trypan blue exclusion for each experimental condition: it was consistently >98%. Dexamethasone (Sigma) and N-monomethyl-L-arginine (L-NMMA: 100 μM, Cayman Chemical, Ann Arbor, Mich.) were used as positive controls for TNF-α and NO inhibition, respectively. Tests were repeated in at least three independent experiments and assays were performed in triplicate.

TNF-α bioactivity was measured in supernatants of cell cultures by standard cytotoxicity assay using L929 cells and recombinant human TNF-α (Sigma) as standard. The detection limit of the bioassay was 20 pg/mL. IL-6 was measured using a commercial murine enzyme-linked immunosorbent assay (ELISA: RPN 2714, Amersham, Little Chalfont, UK).

NO is rapidly oxidized to nitrite in culture medium, and nitrite ($NO_2^-$) concentration is an indicator of NO production. Cell-free culture supernatants were mixed with equal amounts of Griess reagent (1% sulfanilamide, 0.1% naphtylethylenediamide in 2.5% phosphoric acid) in wells of 96-well ELISA plates. Samples were incubated at room temperature for 10 min and absorbance was measured at 540 nm with the use of a microplate reader. Nitrite As concentrations were calculated using a sodium nitrite standard curve.

cAMP accumulation in N9 cells was measured as previously described. Briefly, cells in six-well plates were co-incubated at 37° C. with (1) medium; (2) forskolin (100 μM); (3) LPS (10 ng/mL)+IFN-γ (1 U/mL); (4) α-MSH(1-13) (SEQ ID NO: 3) or a-MSH(11-13) (SEQ ID NO: 1) (1, 10, 50 µM); (5) LPS+IFN-γ and either α-MSN (1-13) (SEQ ID NO: 3) or α-MSH(11-13) (SEQ ID NO: 1) (10 µM). Reactions were stopped after 3 min by aspirating supernatants, immediately adding 1 mL ethanol at −20° C. and freezing. cAMP content in the ethanol-soluble fraction was measured using an enzyme immunoassay kit (Amersham).

Total cellular RNA was extracted from $10^6$ adherent microglial cells plated in six-well tissue culture plates (Corning). Electrophoresis of RNA samples (10 µg/lane) was performed in 1% agarose/2.2 M formaldehyde gels and the gels subsequently blotted onto nylon filters by capillary action and baked for 2 h before prehybridization. The cDNA fragments encoding murine TNF-α and mouse macrophage iNOS were $^{32}$P-labeled using the Ready-To-Go DNA Labeling Kit (Pharmacia, Uppsala, Sweden) before hybridization of nylon filters and autoradiography. Blots were subsequently rehybridized with human glyceraldehyde-3-phosphate dehydrogenase (G-3-PDH) cDNA probe as an internal control (Clontech Laboratories, Inc., Palo Alto, Calif.).

Microglia were plated in 24-well plates at a concentration of $2\times10^5$ cells/ml and α-MSH production was determined in cell-free supernatants after 24 h incubation with LPS, 10 ng/mL; IFN-γ, 1 U/mL; and LPS 10 ng/ml+IFN-γ, 1 U/mL, α-MSH was measured with a double antibody radioimmunoassay (Euro-Diagnostica AB, Malmo, Sweden). The sensitivity of the assay is 0.5 pg/mL and cross-reactivity with other POMC peptides (ACTH(1-24) (SEQ ID NO: 11), ACTH(1-39) (SEQ ID NO: 9), β-MSH, γ-MSH) is <0.002%.

Microglia as above in RPMI 1640 medium supplemented with 10% FBS were pre-incubated overnight with rabbit anti-α-MSH (SEQ ID NO: 3) produced by resting microglia during the overnight adherence period. After preincubation, the medium was removed and cells co-incubated with LPS 10 ng/mL, IFN-γ 1 U/mL or LPS+IFN-γ diluted in 1 mL RPMI 1640 medium (10% FBS) containing the same rabbit anti-α-MSH antibody concentration used during pre-incubation. The cell-free supernatants were removed after a 24-h incubation and assayed for TNF-α, IL-6, and nitrite. Control samples were treated with rabbit IgG at the same dilution.

Effects of melanocortin peptides on cytokine and NO production were evaluated by repeated measures analysis of variance followed by Dunnet's test for specific comparisons. Probability values less than 0.05 were considered significant.

Figure 19:
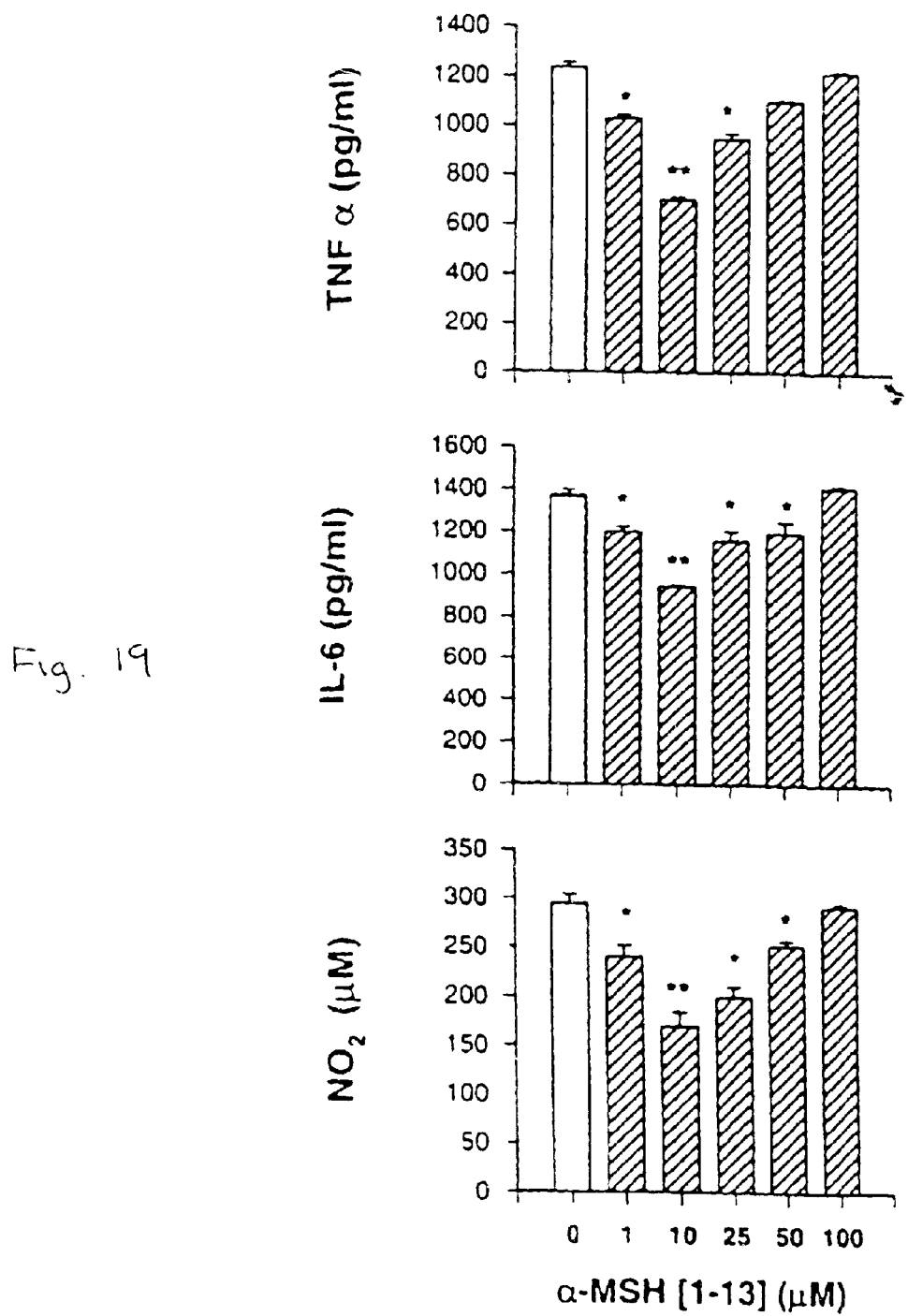
FIG. 19 shows the relative change in concentrations of NO$^-_2$, IL-6 and TNF-α as a function of α-MSH(11-13) (SEQ ID NO: 1) concentration in activated microglia.
Figure 20:
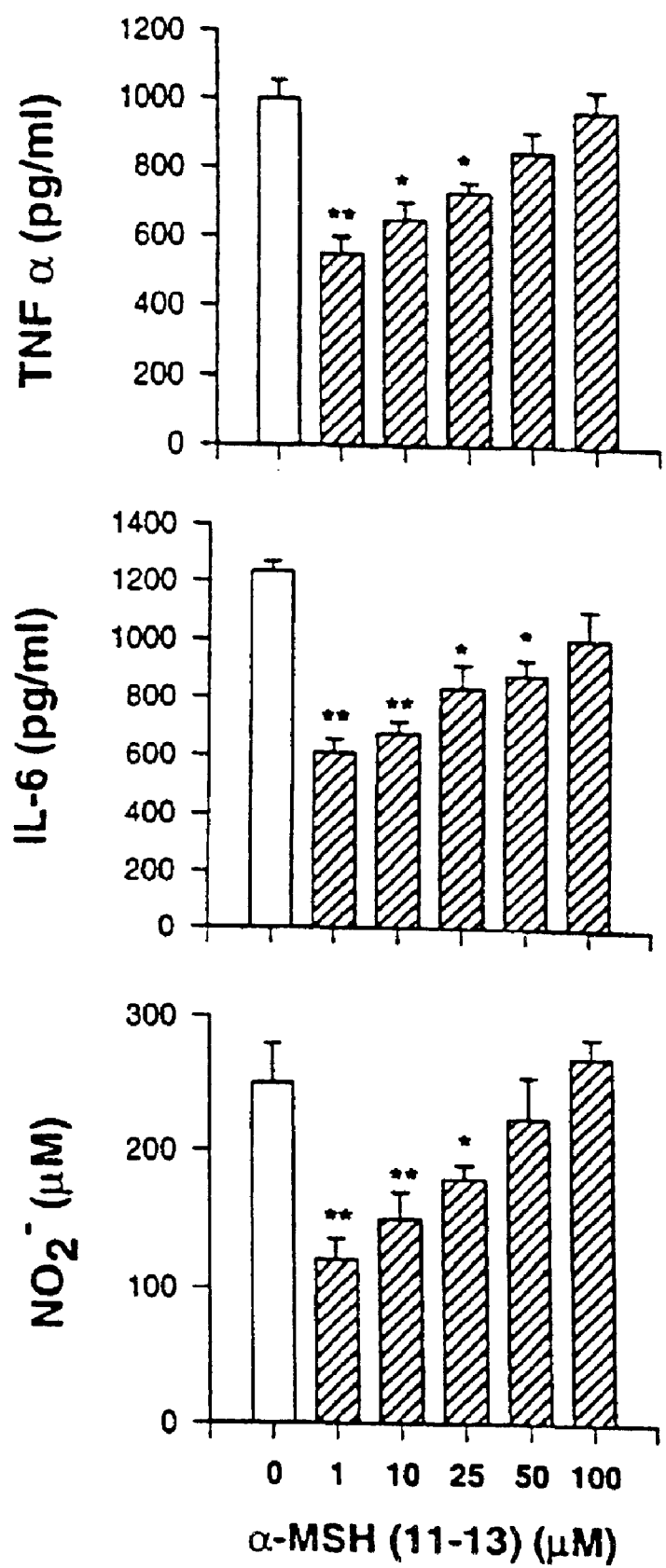
FIG. 20 shows the relative change in concentrations of NO$^-_2$, IL-6 and TNF-α as a function of α-MSH(1-13) (SEQ ID NO: 3) concentration in activated microglia.
Figure 21:
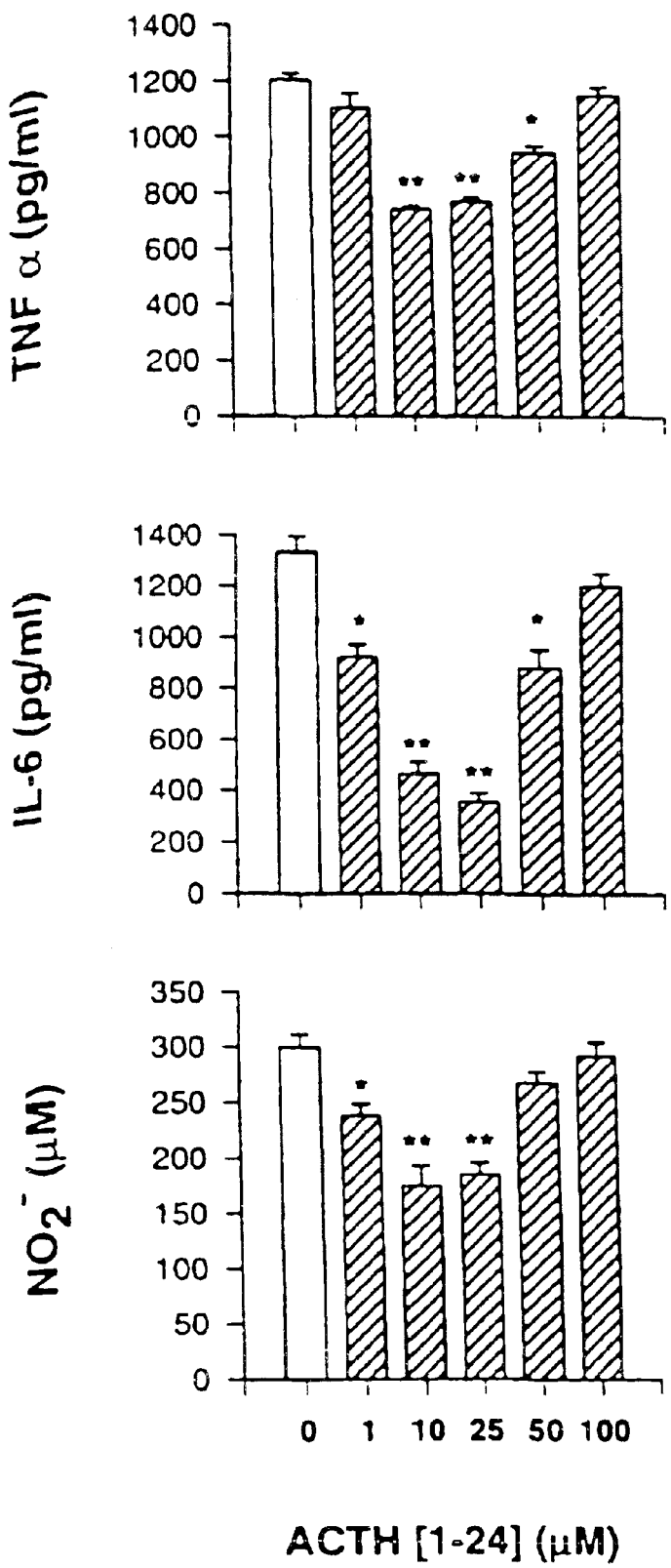
FIG. 21 shows the relative change in concentrations of NO$^-_2$, IL-6 and TNF-α as a function of ACTH(1-24) (SEQ ID NO: 12) concentration in activated microglia.
Figure 22:
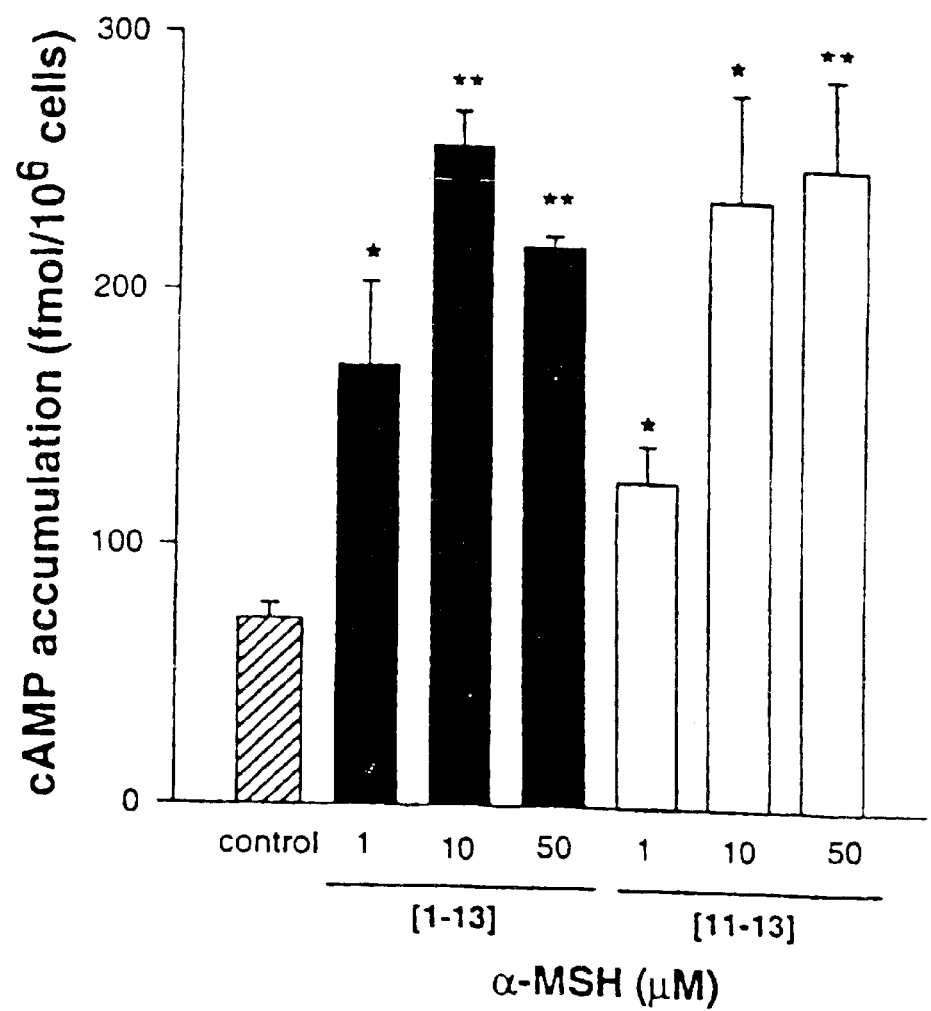
FIG. 22 shows the relative accumulation of cAMP as a function of α-MSH(1-13) (SEQ ID NO: 3) and α-MSH(11-13) (SEQ ID NO: 1) concentration in resting microglia.
Figure 23:
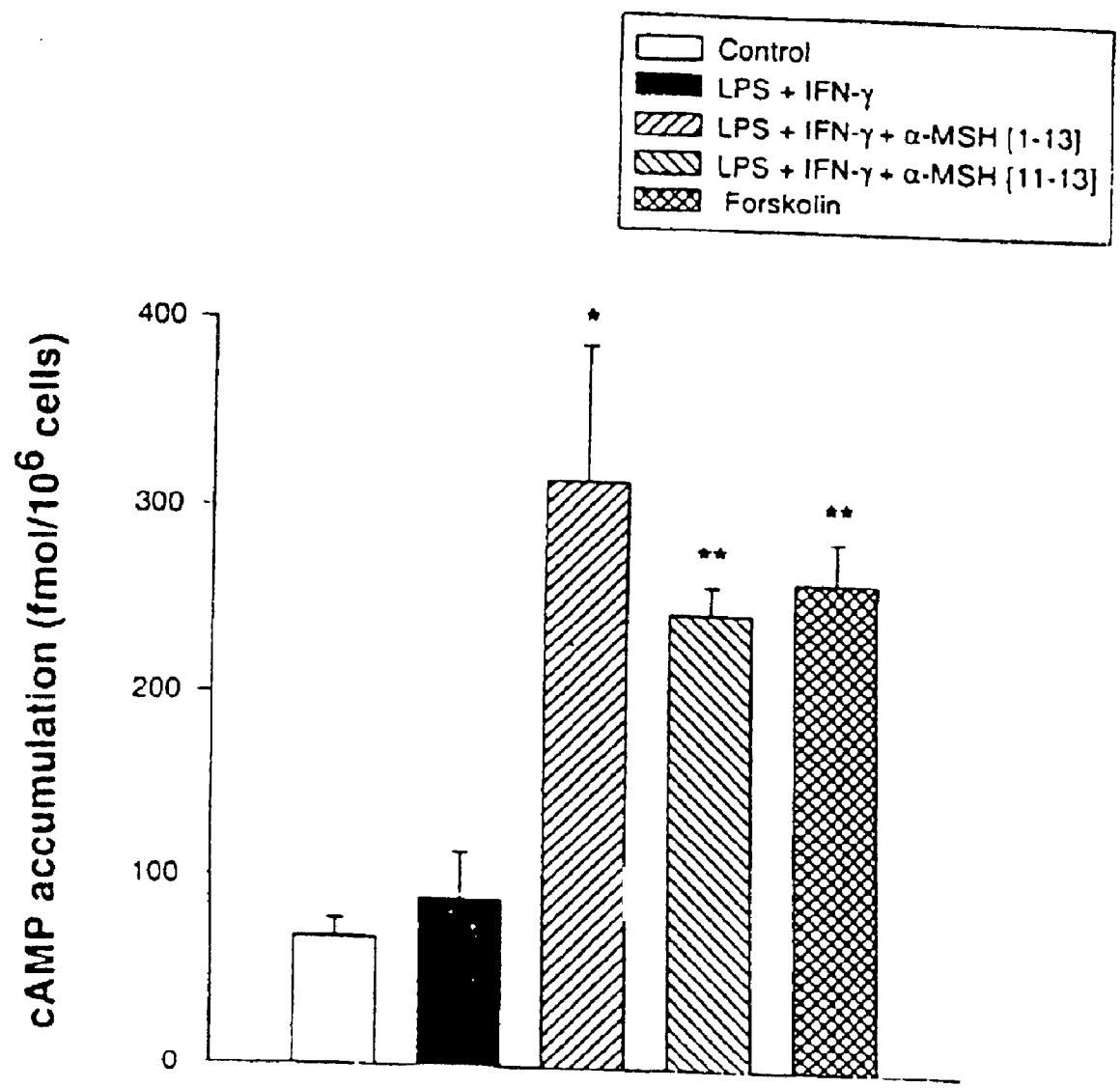
FIG. 23 shows the relative change in concentrations of NO$^-_2$, IL-6 and TNF-α as a function of α-MSH(11-13) (SEQ ID NO: 1) microglia co-incubated with LPS+IFN-α.
Figure 24:
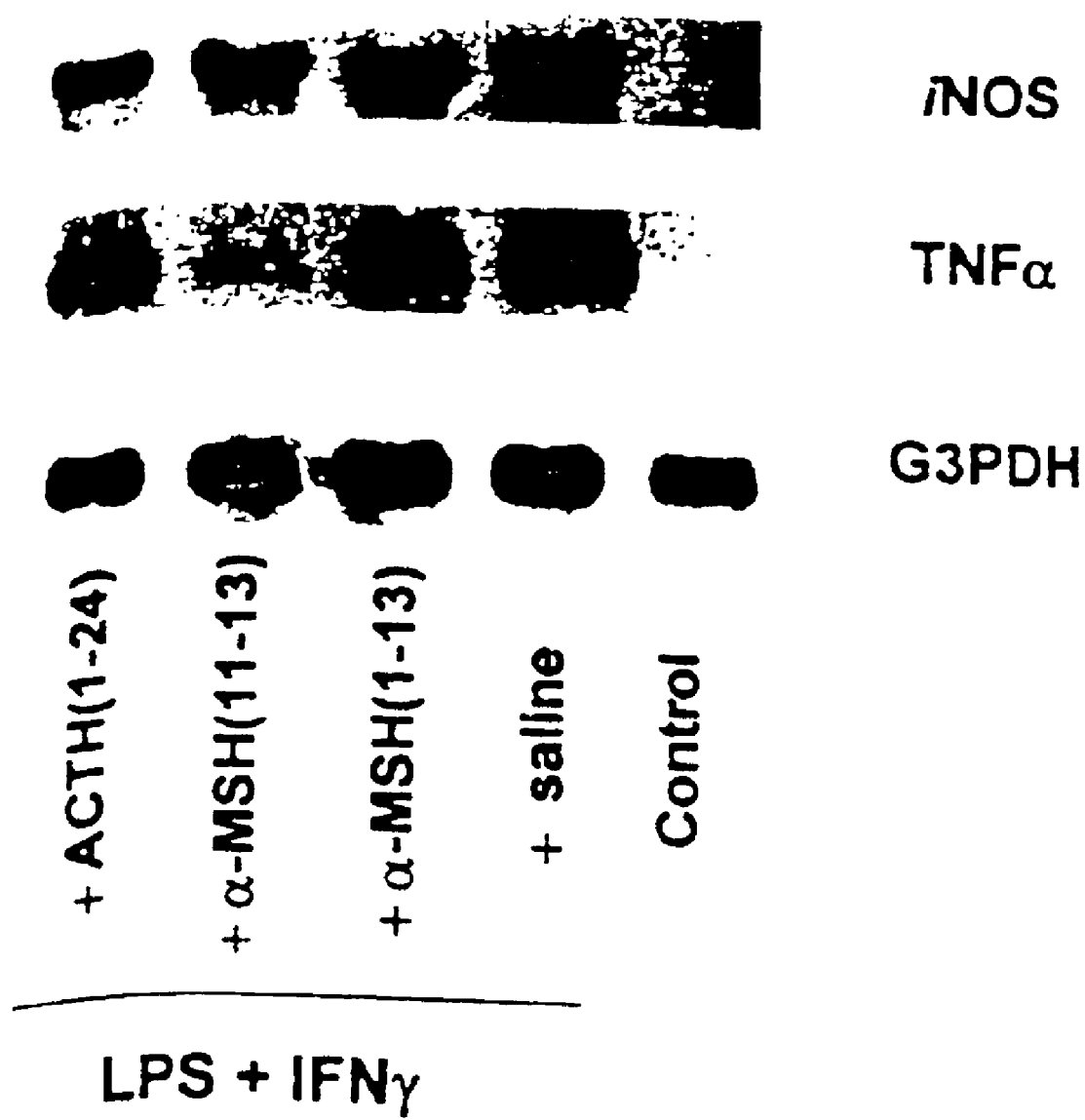
FIG. 24 is a Northern Blot showing the inhibitory influences of melanocortin peptides (ACTH(1-24) (SEQ ID NO: 12), α-MSH(1-13) (SEQ ID NO: 3), α-MSH(11-13) (SEQ ID NO: 1)) on TNF-α and NO$^-_2$ production in activated microglia.

As is shown in FIG. 19 micromolar concentrations of α-MSH(1-13) (SEQ ID NO: 3) significantly reduced IL-6 and $NO_2^-$ levels in microglia stimulated with LPS+IFN-γ for 24 hr. More particularly, α-MSH(1-13) (SEQ ID NO: 3) reduced the production of TNF-α, IL-6 and $NO_2^-$ by 43, 31 and 42% respectively. FIG. 20 shows that α-MSH(1-13) (SEQ ID NO: 3) reduced the production of TNF-α, IL-6 and $NO_2^-$ by 45, 50 & 40% respectively. FIG. 21 shows that ACTH(1-24) reduced the production of TNF-α, IL-6 and $NO_2^-$ in microglia by 38, 65 and 41% respectively. FIGS. 22 and 23 shows that incubation of microglia with α-MSH(1-13) (SEQ ID NO: 3) and α-MSH(11-13) (SEQ ID NO: 1) increased cAMP accumulation in resting cells and cells cancubated with LPS+IFN-γ. FIG. 24 shows further that the magnitude of cAMP accumulation induced by α-MSH peptides was comparable to that caused by forskolin.

Figure 25:
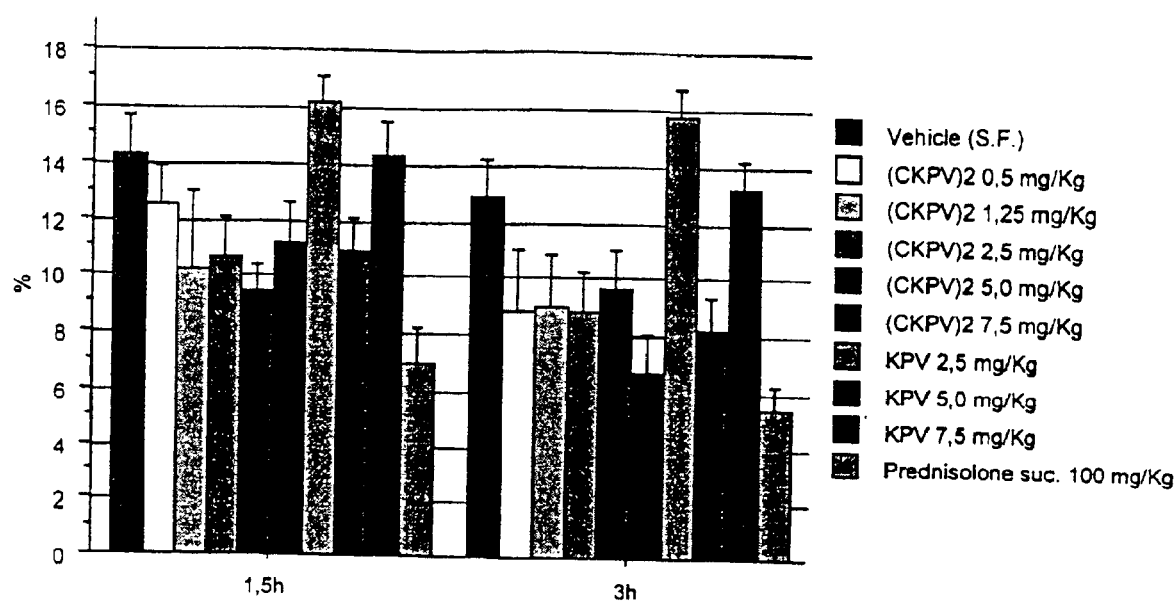
FIG. 25 illustrates the anti-inflammatory effects of the KPV peptide (SEQ ID NO: 1), KPV dimer (SEQ ID NO: 4) and prednisolone on edema induced in the hind paw of mice by the injection α-carageenan as a function of time.

As shown in FIG. 25, Northern blot analysis suggests that the inhibitory influence of melanocortin peptides α-MSH(1-13) (SEQ ID NO: 3), α-MSH(11-13) (SEQ ID NO: 1) ACTH(1-24), (SEQ ID NO: 12) on TNF-α and $NO_2^-$ release was likely caused by the inhibition of mRNA transcription for TNF-α and iNOS.

These results suggest that the anti-inflammatory activity of the α-MSH peptides is associated with a reduction in the cytokines connected to the inflammatory response. LPS and IFN-γ are signaling molecules that stimulate inflammation by increasing production of cytokines such as TNF-α, IL-6, IL-8, and IL-1. During the resultant inflammatory response, there is a marked increase in production of NO. These results show that microglial cells pre-treated with α-MSH(1-13) (SEQ ID NO: 3), α-MSH(11-13) (SEQ ID NO: 1), or ACTH(1-24) (SEQ ID NO: 12) prior to addition of LPS and IFN-γ display a substantial decrease in production of TNF-α, IL-6, and NO. α-MSH(1-13) (SEQ ID NO: 3) was most effective at inhibiting cytokine formation at 10 µM, α-MSH (11-13) (SEQ ID NO: 3) was most effective at 1 µM, and ACTH(1-24) (SEQ ID NO: 12) was most effective at 10–25 µM. All three were ineffective at concentrations higher than 50 µM. When cells were incubated with anti-α-MSH antibodies before and during treatment with LPS and IFN-γ, subsequent treatment with α-MSH peptides had no effect on cytokine production. This verifies that the reduction in TNF-α, NO, or IL-6 seen in the first experiment was directly attributable to α-MSH. Northern blot analysis showed that treatment of cells with α-MSH(1-13) (SEQ ID NO: 3) or α-MSH(11-13) (SEQ ID NO: 1) prior to treatment with LPS and IFN-γ caused a decrease in transcription levels for both TNF-α and iNOS (inducible NO synthase). These results suggest that the α-MSH peptides exert their anti-inflammatory effects in part by preventing extracellular signals, such as LPS and IFN-γ, from inducing production of pro-inflammatory cytokines, perhaps by blocking signaling pathways that lead to transcription of these cytokines. Experiments were also performed that showed microglial cells produce α-MSH (SEQ ID NO: 1) naturally upon stimulation with LPS and IFN-γ, meaning that this peptide sequence is a normal part of the complicated process of inflammation regulation.

After assessing the effects of the α-MSH peptides on production of pro-inflammatory cytokines, experiments were run to analyze their effects on cAMP accumulation. One of the first events to occur during the inflammatory response is a decrease in intracellular cAMP levels. The ability of the α-MSH peptides to induce cAMP accumulation was measured both alone and in conjunction with LPS and IFN-γ. Both α-MSH(1-13) (SEQ ID NO: 3) and α-MSH (11-13) (SEQ ID NO: 3), induced cAMP accumulation at concentrations as low as 1 µM. α-MSH(1-13) (SEQ ID NO: 1) exhibiting its strongest effect at 10 µM, while α-MSH (11-13) (SEQ ID NO: 3) exhibited its strongest effect at 50 µM. At all concentrations tested, the observed accumulation of cAMP was higher than in cells treated with forskolin. When cells were treated with the α-MSH peptides in conjunction with LPS and IFN-γ, there was again a marked increase in cAMP accumulation. α-MSH(1-13) (SEQ ID NO: 3) was the more effective of the two α-MSH peptides, but α-MSH(11-13) (SEQ ID NO: 1) was also able to induce an accumulation similar to that seen in the presence of forskolin. These results suggest that the α-MSH peptides exert their anti-inflammatory effect in part by increasing accumulation of cAMP, thus preventing the decrease in cAMP that accompanies the first steps of the inflammatory response. The results of example 9 provide several possible mechanisms by which the α-MSH peptide sequences appear to prevent inflammation, and again suggest a role for these peptides in the treatment of inflammation in general, and sinusitis in particular.

EXPERIMENT 10

Experiment 10 suggests that preferred compositions according to the invention are comparable to prednisolone for reducing inflammation and accordingly, may serve as therapeutic replacement of prednisolone for the treatment of sinusitis. Experiment 10 compares the anti-inflammatory effects of KPV (SEQ ID NO: 1) and the KPV dimer (also referred to as (CKPV)$_2$) (SEQ ID NO: 4) in reducing edema in the hind paw of male ICR CD-1 mice injected with λ-Carrageenan. A total of 162 male ICR CD-1 mice were used in three different experiments. Each mouse received a single subcutaneous injection (20 μl) of a carrageenan solution (0.125% in saline) in each hind paw to induce edema. Paw volume thickness was measured with a micrometer. In order to compare the anti-inflammatory effectiveness of the peptides according to the invention relative to prednisolone, the 162 mice were divided into 10 groups where each group received the following 200 μl dosages (the number of animals is shown in parenthesis: Saline control (31), (CKPV)$_2$ (SEQ ID NO: 4) 0.5 mg/Kg (7), (CKPV)$_2$ (SEQ ID NO: 4) 1.25 mg/Kg (7), (CKPV)$_2$ (SEQ ID NO: 4) 2.5 mg/Kg (16), (CKPV)$_2$ (SEQ ID NO: 4) 5.0 mg/Kg (17), (CKPV)$_2$ (SEQ ID NO: 4) 7.5 mg/Kg (17), KPV (SEQ ID NO: 4) 2.5 mg/Kg (9), KPV (SEQ ID NO: 1) 5.0 mg/Kg (17), KPV (SEQ ID NO: 1) 7.5 mg/Kg (24) and prednisolone suc. 100 mg/Kg (17). The experiment was run for three hours and paw pad thickness was measured at 1.5 hr and 3 hr following injection of the anti-inflammatory agents. The results of this experiment are shown in FIG. 25. FIG. 25 shows that dosages of (CKPV)$_2$ (SEQ ID NO: 4) at 1.25 mg/Kg, 2.5 mg/Kg, 5.0 mg/Kg, and 7.5 mg/Kg and the dosage of KPV (SEQ ID NO: 1) (SEQ ID NO: 1) at 5.00 mg/Kg, each reduced paw edema by approximately 15–30% versus the approximate 50% reduction in paw edema by prednisolone. Although this experiment suggests that prednisolone is more effective at reducing inflammation than the peptides according to the invention, as taught in the earlier sections, the peptides according to the invention reduce inflammation without the immuno-suppresive and other deleterious side-effects of steroidal anti-inflammatories such as prednisolone.

EXAMPLE 11

A middle age male patient presents complaining of chronic sinus headaches, recurring low grade flu like symptoms and post nasal drip. The patient's history indicates he has had a broad range of allergies to common, airborne allergens since childhood. Blood samples show clinically acceptable white cell counts. The patient is prescribed a pharmacologically effective oral dosage of erythromycin and a pharmacologically effective oral dosage of α-MSH.

Although the invention has been described with reference to preferred embodiments and specific examples, it will be readily appreciated by those skilled in the art that many modifications and adaptations of the invention are possible without deviating from the spirit and scope of the invention. Thus, it is to be clearly understood that this description is made only by way of example and not as a limitation on the scope of the invention as claimed below.

What is claimed is:

1. A composition for the treatment of sinusitis comprising a therapeutically effective amount of a peptide having a C-terminal amino acid sequence KPV selected from the group of peptides consisting of: KPV (SEQ ID NO: 1), VKP-Ac-CC-Ac-KPV (SEQ ID NO: 4), HFRWGKPV (SEQ ID NO: 2) and SYSMEHFRWGKPV (SEQ ID NO: 3) in combination with a therapeutically effective amount of a decongestant/antihistamine.

2. The composition of claim 1 wherein said decongest/antihistamine is selected from the group consisting of: pseudoephedrine, phenylephrine, phenylpropanolamine, chlorpheniramine, bromopheniramine, pheniramine and loratidine.

3. The composition of claim 1 further comprising a therapeutically effective amount of an antibiotic.

4. The composition of claim 3 wherein said antibiotic is selected from the group consisting of: amoxicillin, ampicillin, azithramycin, erythromycin, nafcillin, penicillin, amoxicillin/clavulanate potassium, cefuroxime axetil, cepodoxime proxetil, clarithromycin, and azithramycin.

5. The composition of claim 1 further comprising a therapeutically effective amount of a glucocorticosteroid.

6. The composition of claim 5 wherein said glucocorticosteroid is selected from the group consisting of: betamethasone, budesponide, cortisone, dexamethasone, hydrocortisone, methylprednisone, prednisone, and triamcinolone.

7. The composition of claim 1 further comprising a therapeutically effective amount of a fungicide.

8. The composition of claim 7 wherein said fungicide is selected from the group consisting of: itraconazole, econazole, ketoconazole, miconazole and fluconazole.

9. The composition of claim 1 further comprising a carrier.

10. The composition of claim 9 wherein the concentration of said peptide is at least $10^{-12}$.

11. The composition of claim 10 wherein the carrier is selected from the group consisting of: saline, phosphate buffered saline, gelatin, maltodextrin, cellulose, microcrystalline cellulose, methyl cellulose, carboxymethyl cellulose, and hydroxymethyl cellulose with glycerin.

* * * * *

UNITED STATES PATENT AND TRADEMARK OFFICE
CERTIFICATE OF CORRECTION

PATENT NO. : 7,115,574 B2
APPLICATION NO. : 10/015055
DATED : October 3, 2006
INVENTOR(S) : Anna P. Catania and James M. Lipton It is certified that error appears in the above-identified patent and that said Letters Patent is hereby corrected as shown below:

Field (54) of the face page should read:

COMPOUND AND METHOD FOR THE TREATMENT OF SINUSITIS

At column 1, lines 3-5, the title should be replaced to read:

COMPOUND AND METHOD FOR THE TREATMENT OF SINUSITIS

Signed and Sealed this

Twenty-sixth Day of December, 2006

JON W. DUDAS
*Director of the United States Patent and Trademark Office*